US006884878B2

(12) United States Patent
Borovsky et al.

(10) Patent No.: US 6,884,878 B2
(45) Date of Patent: Apr. 26, 2005

(54) NEUROPEPTIDES AND THEIR USE FOR PEST CONTROL

(75) Inventors: Dov Borovsky, Vero Beach, FL (US); Arnold De Loof, Leuven (BE); Peter Verhaert, Vorselaar (BE)

(73) Assignee: University of Florida Research Foundation, Inc., Gainesville, FL (US)

( * ) Notice: Subject to any disclaimer, the term of this patent is extended or adjusted under 35 U.S.C. 154(b) by 5 days.

(21) Appl. No.: 10/062,623

(22) Filed: Jan. 31, 2002

(65) Prior Publication Data

US 2003/0108520 A1 Jun. 12, 2003

Related U.S. Application Data

(63) Continuation-in-part of application No. 09/295,849, filed on Apr. 21, 1999, now abandoned.

(51) Int. Cl.[7] .......................... C07H 21/02; C07H 21/04; C12P 21/06; C12N 7/00; C12N 5/06
(52) U.S. Cl. .................... 536/23.5; 536/23.1; 536/23.4; 435/69.1; 435/235.1; 435/329; 514/44
(58) Field of Search ................................ 536/23.1, 23.4, 536/23.5; 514/44; 435/329, 69.1, 235.1; 530/300; 426/565

(56) References Cited

U.S. PATENT DOCUMENTS

| | | |
|---|---|---|
| 4,266,074 A | 5/1981 | Fujimoto et al. |
| 4,714,763 A | 12/1987 | Theodoropulos |
| 4,983,390 A | 1/1991 | Levy |
| 4,985,251 A | 1/1991 | Levy |
| 5,011,909 A | 4/1991 | Borovsky et al. |
| 5,093,362 A | 3/1992 | Milner et al. |
| 5,130,253 A | 7/1992 | Borovsky et al. |
| 5,141,744 A | 8/1992 | Chang et al. |
| RE34,402 E | 10/1993 | Williams |
| 5,250,515 A | 10/1993 | Fuchs et al. |
| 5,259,153 A | 11/1993 | Olive et al. |
| 5,273,749 A | 12/1993 | Bok et al. |
| 5,344,821 A | 9/1994 | Kingan et al. |
| 5,348,665 A | 9/1994 | Schulte et al. |
| 5,358,934 A | 10/1994 | Borovsky et al. |
| 5,399,344 A | 3/1995 | Yang et al. |
| 5,428,147 A | 6/1995 | Barker et al. |
| 5,439,821 A | 8/1995 | Borovsky et al. |
| 5,459,130 A | 10/1995 | Borovsky et al. |
| 5,501,976 A | 3/1996 | Borovsky et al. |
| 5,508,264 A | 4/1996 | Bradfisch et al. |
| 5,513,465 A | 5/1996 | Demarest et al. |
| 5,522,171 A | 6/1996 | Mandeville |
| 5,527,883 A | 6/1996 | Thompson et al. |
| 5,567,430 A | 10/1996 | Levy |
| 5,604,121 A | 2/1997 | Hilder et al. |
| 5,612,047 A | 3/1997 | Duffy et al. |
| 5,629,196 A | 5/1997 | Borovsky et al. |
| 5,656,260 A | 8/1997 | Boden et al. |
| 5,670,145 A | 9/1997 | Wright |
| 5,676,846 A | 10/1997 | Vickell et al. |
| 5,676,958 A | 10/1997 | Emerson et al. |
| 5,683,687 A | 11/1997 | Marin et al. |
| 5,688,764 A | 11/1997 | Johnson et al. |
| 5,693,344 A | 12/1997 | Knight et al. |
| 5,713,153 A | 2/1998 | Cook et al. |
| 5,714,191 A | 2/1998 | Hatton et al. |
| 5,737,870 A | 4/1998 | Thind |
| 5,741,669 A | 4/1998 | Krapcho et al. |
| 5,749,168 A | 5/1998 | Chrysanthis |
| 5,753,615 A | 5/1998 | Thorpe et al. |
| 5,792,750 A | 8/1998 | Borovsky et al. |
| 5,800,811 A | 9/1998 | Hall et al. |
| 5,824,328 A | 10/1998 | Levy |
| 5,840,293 A | 11/1998 | Nacht et al. |
| 5,846,553 A | 12/1998 | Levy |
| 5,849,525 A | 12/1998 | Hediger |
| 6,413,530 B1 | 7/2002 | Borovsky et al. |

FOREIGN PATENT DOCUMENTS

| | | |
|---|---|---|
| EP | 0412595 A1 | 2/1991 |
| EP | 0 682 115 A1 | 11/1995 |
| JP | 01 226898 | 9/1989 |
| JP | 07 188282 | 7/1995 |
| WO | 9321217 | 4/1992 |
| WO | WO 94/13698 A1 | 6/1994 |
| WO | WO 95/24423 A1 | 9/1995 |
| WO | WO 98/21348 A1 | 5/1998 |
| WO | WO 99/51721 A1 | 10/1999 |

OTHER PUBLICATIONS

U.S. Appl. No. 09/551,738, Borovsky.
U.S. Appl. No. 09/551,737, Borovsky et al.
U.S. Appl. No. 09/296,113, Borovsky.
U.S. Appl. No. 09/295,924, Bennett et al.
U.S. Appl. No. 09/295,846, Borovsky.
Allefs, S. et al "Erwinia soft rot resistance of potato cultivars transformed with a gene construct coding for antimicrobial peptide Cecropin B is not altered" *American Potato J.*, 1995, 72:437–445.
Bordusa, F. and H–D. Jakubke "the Specificity of Prolyl Endopeptidase from *Flavobacterium meningoseptum*: Mapping the S' Subsites by Positional Scanning via Acyl Transfer" *Bioorganic & Medicinal Chemistry*, 1998, 6:1775–1780.
Borovsky, D. and F. Mahmood "Feeding the mosquito *Aedes aegypti* with TMOF and its analogs; effect on trypsin biosynthesis and egg development" *Regulatory Peptides*, 1995, 57:273–281.
Borovsky, D. et al. "Development of Specific RIA and ELISA to Study Trypsin Modulating Oostatic Factor in Mosquitos" *Archives of Insect Biochemistry and Physiology*, 1992, 21:13–21.

(Continued)

Primary Examiner—Joseph Woitach
(74) Attorney, Agent, or Firm—Saliwanchik, Lloyd & Saliwanchik

(57) ABSTRACT

The present invention discloses novel pest control compounds comprising NPF polypeptides and methods for using such compounds in the control of pests.

69 Claims, 3 Drawing Sheets

OTHER PUBLICATIONS

Borovsky, D. et al. "Mosquito Oostatic Hormone" *Insect Neuropeptidases: Chemistry, Biology Action*, 1991, 135–142.

Bylemans, D. et al. "Immunolocalization of the Oostatic and Prothoracicostatic Peptide, Neb–TMOF, in Adults of the fleshfly, *Neobellieria bullata*" *General and Comparative Endocrinology*, 1996, 103:273–280.

Bylemans, D. et al. "Neb–colioostatin, a second folliculostatin of the grey fleshfly, *Neobellieria bullata*" *Eur. J. Biochem.*, 1995, 228:45–49.

Bylemans, D. et al. "Sequencing and characterization of trypsin modulating oostatic factor (TMOF) from the ovaries of the grey fleshfly, *Neobellieria* (*Sarcophage*) *bullata*" *Reg. Peptides*, 1994, 50:61–72.

Bosch, D. et al. "A trout growth hormone is expressed, correctly folded and partially glycosylated in the leaves but not the seeds of transgenic plants" *Transgenic Res.*, 1994, 3:304–310.

Charbonneau, H. "Strategies for Obtaining Partial Amino Acid Sequence Data from Small Quantities (>5nmol) of Pure or Partially Purified Protein" A Practical Guide to Protein and Peptide Purification for Microsequencing, 1989, pp. 15–30.

Chee, M. et al. Accession Nos. P16753, Q69030.

Copley et al. "Expression, processing and secretion of a proteolytically–sensitive insect diuretic hormone . . . " *Biochem.*, 1998, 330:1333–1340.

Dahlen, J.R. et al. "Expression, Purification and Inhibitory Properties of Human Proteinase Inhibitor" *Biochemistry*, 1997, 35:14874–14882.

De Bolle, M. et al. "Antimicrobial peptides from *Mirabilis jalapa* and *Amaranthus caudatus*: expression, processing, localization and biological activity in transgenic tobacco" *Plant Mole. Biol.*, 1996, 31:993–1008.

Deslauriers et al. "Steric Effects of Cis–Trans Isomerism on Neighboring Residues in Proline Oligopeptides: A C–NMR Study of conformational Heterogeneity in Linear Tripeptides" *Biopolymers*, 1979, 18(3):523–538.

Eipper et al. "The Biosynthesis of Neuropeptides: Peptide Amidation" *Annul Rev. Neurosci.*, 1992, 15:57–85.

Gauthier et al. "Direct Submission" *Plant Physiol.*, 1995, 108:1341. (abstract/sequence only).

Henderson et al. "Physicochemical studies of biologically active peptides by low–temperature reversed–phase high-performance liquid chromatography" *Chemical Abstracts*, May 21, 1990, 112(21), abstract No. 192024, abstract only.

Hightower, R. et al. "The expression of cecropin peptide in transgenic tobacco does not confer resistance to *Pseudomonas syringae* pv *tabaci*" *Plant Cell Reports*, 1994, 13:295–299.

Hlavacek et al. "The C–Terminus Shortened Analogs of the Insect Peptide Oostatic Hormone with Accelerated Activity" *Bioorg. Chem.*, Oct. 1998, 26:131–140.

Hlavacek et al. "Synthesis, radiolabeling and biological activity of peptide oostatic hormone and its analogues" *J. Peptide Res.*, 1997, 50:153–158.

Hua, Y–J. and J. Koolman "An ecdysiostatin from flies" *Regulatory Peptides*, 1995, 57:263–271.

Janssen, I. et al. "Biological Activity of Structural Analogs and Effect of Oil as a Carrier of Trypsin Modulating Oostatic Factor of the Gray Fleshfly *Neobellieria bullata*" *Peptides*, 1998, 19(4):627–634.

Kolaskar, A.S. and V. Ramabrahmam, "Conformational properties of pairs of amino acids" *Int. J. Peptide Protein Res.*, 1983, 22:83–91.

Ladram et al. "Characterization of receptors for thyrotropin–releasing hormone–receptors potentiating peptide on rat anterior pituitary membranes" *J. Biol. Chem.*, 1992, 267(36):25697–25702.

Lin, Y. et al. "Structure, Expression and Hormonal Control of Genes from the Mosquito, *Aedes aegypti*, Which Encode Proteins Similar to the Vitelline Membrane Proteins of *Drosophila melanogaster*" *Dev. Biology*, 1993, 155:558–568.

Masoud, S.A. et al. "Expression of a cysteine proteinase inhibitor (oryzacystatin–I) in transgenic tobacco plants" *Plant Molecular Biology*, 1993, 21:655–663.

Masuda, N. et al. "Primary structure of protein moiety of *Penicillin notatum* phospholipase B deduced from the cDNA" *Eur. J. Biochem.*, 1991, 202:783–787.

Meissner, H. et al. Accession No. O33838, Nov. 1997.

Menn et al. "Insect Neuropeptides: Potential New Insect Control Agents" *J. Agric. Food Chem.*, 1989, 37:271–274.

Menzel, D. et al. Accession No. P48579, 1995.

Merkler et al. "C–Terminal amidated peptides: Production by the in vitro enzymatic amidation of glycine–extended peptides and the importance of the amide to bioactivity" *Enzyme*, 1994, 16(6):450–456.

Narberhaus et al. "The *Bradyrhizobium japonicum* rpoH1 gene encoding a sigma 32–likeprotein is part of a unique heat shock gene cluster together with groESL1 and three small heat shock genes" *J. Bacteriol.* 1996, 178:5337–5346 (abstract/sequence only).

Nauen et al. "TMOF–like factor controls the biosynthesis of serine proteases in the larval gut of *Heliothis virescens*" *Arch. Insect. Biochem.*, 2001, 47:169–180.

Okada et al. "Synthesis of bradykinin fragments and their effect on pentobarbital sleeping time in mouse" *Chemical Abstracts*, Nov. 7, 1977, 87(19), abstract No. 146142, abstract only.

Okamoto, M. et al. "Enhanced Expression of an Antimicrobial Peptide Sarcotoxin IA by GUS Fusion in Trangenic Tobacco Plants" *Plant Cell Physiol.*, 1996, 39:57–63.

Pang, S. et al. "Expression of a gene encoding a scorpion insectotoxin peptide in yeast, bacteria and plants" *Gene*, 1992, 116:165–172.

Pauletti et al. "Structural requirements for intestinal absorption of peptide drugs" *J. Controled Rel.*, 1996, 41:3–17.

Rayne, R.C. and M. O'Shea "Inactivation of Neuropeptide Hormones (AKH I and AKH II) Studied in Vivo and In Vitro" *Insect Biochem. Molec.*, 1992, 22(1):25–34.

Rogina, B. et al. Accession Nos. P24342, Q90780, 1992.

Rourke et al. "Heterologous Expression of Human Colecystokinin in *Saccharomyces cerevisiae*" *J. Biol. Chem.*, 1997, 15:9720–9727.

Rudinger "Characteristics of the amino acids as components of a peptide hormone sequence" Jun. 1976, pp. 1–7, In Peptide Hormones, Parsons (ed.), University Park press, Baltimore.

Schartau, W. et al. Accession No. X16893, 1990.

Schwartz, J.C. et al. "Biological Inactivation of Enkephalins and the Role of Enkephalin–Dipeptidyl–Carboxypeptidase ("Enkephalinase") as Neuropeptidase" *Life Sciences*, 1981, 29:1715–1740.

Shibnev et al. "Synthesis of monomers that are triplets of the "crystalline" part of the collagen molecule" *Chemical Abstracts,* Jun. 23, 1969, 70(25):392–397, abstract only.

Sober, H.A. "Handbook of Biochemistry" The Chemical Rubber Co., Cleveland, Ohio, 1968, p. C70.

Southwick, F.S. and D.L. Purich "Inhibition of Listeria Locomotion by Mosquito Oostatic Factor, a Natural Oligoproline Peptide Uncoupler of Profilin Action" *Infection and Immunity,* 1995, 63(1):182–190.

Stone, S. et al. Accession No. P11493, 1997.

Taylor, M. "Trypsin Isolated from the Midgut of the Tobacco Hornworm, *Manduca sexta,* I inhibited by Synthetic Pro–peptides in Vitro" *Biochem. Res. Comm.,* 1997, 235:606–609.

Tykva, R. et al. "The fate of an oostatic peptide or its analogs including metabolites in insects Diptera and Orthoptera and its transformation to the next generation" *Chemical Abstracts,* 132(26), abstract No. 345576.

Vaeck, M. et al. "Transgenic plants protected from insect attack" *Nature,* 1987, 328:33–37.

Voit, R. and G. Feldmaier–Fuchs "Arthropod Hemocyanins. Molecular Cloning and Sequencing of cDNAs Encoding the Tarantula Hemocyanin Subunits a and e" *J. Biol. Chem.,* Nov. 15, 1990, 265:19447–19452.

Youn, H. et al. Accession No. Q9JP84, 1998.

Borovsky, Dov (1985) "Isolation and Characterization of Highly Purified Mosquito Oostatic Hormone" *Archives of Insect Biochemistry and Physiology* 2:333–349.

Borovsky, Dov (1988) "Oostatic Hormone Inhibits Biosynthesis of Midgut Proteolytic Enzymes and Egg Development in Mosquitos" *Archives of Insect Biochemistry and Physiology* 7:187–210.

Borovsky, Dov (1990) "Mosquito oostatic factor: a novel decapeptide modulating trypsin–like enzyme biosynthesis in the midgut" *The FASEB Journal* 4:3015–3019.

Borovsky, Dov, D.A. Carlson, P.R. Griffin, J. Shabanowitz, D.F Hunts (1993) "Mass Spectrometry and Characterization of *Aedes aegypti* Trypsin Modulating Oostatic Factor (TMOF) and its Analogs" *Insect Biochem. Molec. Biol.* 23(6):703–712.

Borovsky, Dov, C.A. Powell, J.K. Nayar, J. Edwin Blalock, T.K. Hayes (1994) "Characterization and localization of mosquito–gut receptors for trypsin modulating oostatic factor using a complementary peptide and immunocytochemistry" *The FASEB Journal* 8:350–355.

Curry, W.J., C. Shaw, C.F. Johnston, L. Thim, K.D. Buchanan (1992) "Neuropeptide F: Primary Structure From The Tubellarian, *Artioposthia triangulata*" *Comp. Biochem. Physiol.* 101C(2):269–274.

Duve, Hanne, Alan Thorpe, Ray Neville, Norman R. Lazarus (1981) "Isolation and partial characterization of pancreatic polypeptide–like material in the brain of the blowfly *Calliphora vomitoria*" *J. Biochem.* 197:767–770.

Leung, P.S., C. Shaw, A.G. Maule, L. Thim, C.F. Johnston, G.B. Irvine (1992) "The primary structure of neuropeptide F (NPF) from the garden snail, *Helix aspersa*" *Regulatory Peptides* 41:71–81.

Maule et al. (1991) "Neuropeptide F: a novel parasitic flatworm regulatory peptide from *Moniezia expansa* (Cestoda: cyclophyllidea)" *Parasitology* 102:309–316.

Rajpara, Sanjay M., et al. (1992) "Identification and Molecular Cloning of a Neuropeptide Y Homolog That Produces Prolonged Inhibition in Aplysia Neurons" *Neuron* 9:505–513.

Spittaels, Kurt, Peter Verhaert, Christ Shaw, Richard N. Johnston, Bart Devreese, Jos Van Beeumen, Arnold De Loof (1996) "Insect Neuropeptide F (NPF)–related Peptides: Isolation from Colorado Potato Beetle (*Leptinotarsa decemlineata*) Brain" *Insect Biochem. Molec. Biol.* 26(4):375–382.

Veenstra, J.A., H.M. Romberg–Privee, H. Schooneveld, J.M. Polak (1985) "Immunocytochemical localization of peptidergic neurons and neurosecretory cells in the neuro–endocrine system of the Colorado potato beetle with antisera to vertebrate regulatory peptides" *Histochemistry* 82:9–18.

Verhaert, Peter, Cornelis J. P. Grimmelikhuijzen, Arnold De Loof (1985) "Distinct Localization of FMRFamide– and Bovine Pancreatic Polypeptide–Like Material in the Brain, Retrocerebral Complex and Suboesophageal Ganglion of the Cockroach *Periplaneta americana* L." *Brain Research* 348:331–338.

Rao, R. et al. (1996) "Synthesis and Expression of Genes Encoding Putative Insect Neuropeptide Precursors in Tobacco" *Gene* 175:1–5.

Tortiglione, C. et al. (1999) (Abstract) "New genes for Pest Control" *Genetics and Breeding for Crop Quality and Resistance.*

Tortiglione, C. et al. (1999) "New Genes for Pest Control" *Genetics and Breeding for Crop Quality and Resistance* pp. 159–163.

Berghammer, A.J. et al. "A universal marker for transgenic insects" *Nature ,* 1999, 402:370–371.

Chao, Y–C. et al., "Pest control by fluoresence" *Nature ,* 1996, 380:396–397.

Lange, A.B. et al. "A nonpeptide agonist of the invertebrate receptor for SchistoFLRFamide (PDVDHVFLRFamide), a member of a subfamily of Insect FMRFamide–related peptides" *Proc. Natl. Acad. Sci. USA,* 1995, 92:9250–9253.

Sehgal, D. and Gopinathan, K. "Recombinant *Bombyx mori* nucleopolyhedro–virus harboring green fluorescent protein" *Biotechniques,* 1998, 25(6):997–1006.

NEUROPEPTIDES AND THEIR USE FOR PEST CONTROL

CROSS-REFERENCE TO RELATED APPLICATION

The present application is a continuation-in-part of U.S. application Ser. No. 09/295,849, filed Apr. 21, 1999 now abandoned.

BACKGROUND OF THE INVENTION

Many blood-ingesting pests are known to feed on humans and animals, and many pests are vectors for pathogenic microorganisms which threaten human and animal health, including commercially important livestock, pets and other animals. Various species of mosquitoes, for example, transmit diseases caused by viruses, and many are vectors for disease-causing nematodes and protozoa. Mosquitoes of the genus *Anopheles* transmit *Plasmodium*, the protozoan which causes malaria, a devastating disease which results in approximately 1 million deaths annually. The mosquito species *Aedes aegypti* transmits an arbovirus that causes yellow fever in humans. Other arboviruses transmitted by *Aedes* species include the causative agents of dengue fever, eastern and western encephalitis, Venezuelan equine encephalitis, St. Louis encephalitis, chikungunya, oroponehe and bunyarnidera. The genus *Culex*, which includes the common house mosquito *C. pipiens*, is implicated in the transmission of various forms of encephalitis and filarial worms. The common house mosquito also transmits *Wuchereria bancrofti* and *Brugia malayi*, which cause various forms of lymphatic filariasis, including elephantiasis. *Trypanasoma cruzi*, the causative agent of Chagas' disease, is transmitted by various species of blood-ingesting Triatominae bugs. The tsetse fly (*Glossina* spp.) transmits African trypanosomal diseases of humans and cattle. Many other diseases are transmitted by various blood-ingesting pest species. The order Diptera contains a large number of blood-ingesting and disease-bearing pests, including, for example, mosquitoes, black flies, no-see-ums (punkies), horse flies, deer flies and tsetse flies.

Various pesticides have been employed in efforts to control or eradicate populations of disease-bearing pests, such as disease-bearing blood-ingesting pests. For example, DDT, a chlorinated hydrocarbon, has been used in attempts to eradicate malaria-bearing mosquitoes throughout the world. Other examples of chlorinated hydrocarbons are BHC, lindane, chlorobenzilate, methoxychlor, and the cyclodienes (e.g., aldrin, dieldrin, chlordane, heptachlor, and endrin). The long-term stability of many of these pesticides and their tendency to bioaccumulate render them particularly dangerous to many non-pest organisms.

Another common class of pesticides is the organophosphates, which is perhaps the largest and most versatile class of pesticides. Organophosphates include, for example, parathion, MALATHION, diazinon, naled, methyl parathion, and dichlorvos. Organophosphates are generally much more toxic than the chlorinated hydrocarbons. Their pesticidal effect results from their ability to inhibit the enzyme cholinesterase, an essential enzyme in the functioning of the insect nervous system. However, they also have toxic effects on many animals, including humans.

The carbamates, a relatively new group of pesticides, include such compounds as carbamyl, methomyl, and carbofuran. These compounds are rapidly detoxified and eliminated from animal tissues. Their toxicity is thought to involve a mechanism similar to the mechanism of the organophosphates; consequently, they exhibit similar shortcomings, including animal toxicity.

A major problem in pest control results from the capability of many species to develop pesticide resistance. Resistance results from the selection of naturally-occurring mutants possessing biochemical, physiological or behavioristic factors that enable the pests to tolerate the pesticide. Species of *Anopheles* mosquitoes, for example, have been known to develop resistance to DDT and dieldrin. DDT substitutes, such as MALATHION, propoxur and fenitrothion are available; however, the cost of these substitutes is much greater than the cost of DDT.

There is clearly a longstanding need in the art for pesticidal compounds that are pest-specific, that reduce or eliminate direct and/or indirect threats to human health posed by presently available pesticides, that are environmentally compatible in the sense that they are biodegradable, and are not toxic to non-pest organisms, and have reduced or no tendency to bioaccummulate.

Many pests, including for example blood-inbibing pests, must consume and digest a proteinaceous meal to acquire sufficient essential amino acids for growth, development and the production of mature eggs. Adult pests, such as adult mosquitoes, need these essential amino acids for the production of vitellogenins by the fat body. These vitellogenins are precursors to yolk proteins which are critical components of oogenesis. Many pests, such as house flies and mosquitoes, produce oostatic hormones that inhibit egg development by inhibiting digestion of the protein meal, and thereby limiting the availability of the essential amino acids necessary for egg development.

Serine esterases such as trypsin and trypsin-like enzymes (collectively referred to herein as "TTLE") are important components of the digestion of proteins by insects. In the mosquito, *Aedes aegypti*, an early trypsin that is found in the midgut of newly emerged females is replaced, following the blood meal, by a late trypsin. A female mosquito typically weighs about 2 mg and produces 4 to 6 $\mu$g of trypsin within several hours after ingesting blood meal. Continuous biosynthesis at this rate would exhaust the available metabolic energy of a female mosquito; as a result, the mosquito would be unable to produce mature eggs, or even to find an oviposition site. To conserve metabolic energy, the mosquito regulates TTLE biosynthesis with a peptide hormone named Trypsin Modulating Oostatic Factor (TMOF). Mosquitoes produce TMOF in the follicular epithelium of the ovary 12–35 hours after a blood meal; TMOF is then released into the hemolymph where it binds to a specific receptor on the midgut epithelial cells, signaling the termination of TTLE biosynthesis.

This regulatory mechanism is not unique for mosquitoes; flesh flies, fleas, sand flies, house flies, dog flies and other pests which ingest protein as part of their diet have similar regulatory mechanisms.

In 1985, Borovsky purified an oostatic hormone 7,000-fold and disclosed that injection of a hormone preparation into the body cavity of blood imbibed mosquitoes caused inhibition of egg development and sterility (Borovsky, D. [1985] *Arch. Insect Biochem. Physiol.* 2:333–349). Following these observations, Borovsky (Borovsky, D. [1988] *Arch. Ins. Biochem. Physiol.* 7:187–210) reported that injection or passage of a peptide hormone preparation into mosquitoes inhibited the TTLE biosynthesis in the epithelial cells of the gut. This inhibition caused inefficient digestion of the blood meal and a reduction in the availability of essential amino acids translocated by the hemolymph, resulting in arrested egg development in the treated insect. Borovsky observed that this inhibition of egg development does not occur when the oostatic hormone peptides are inside the lumen of the gut or other parts of the digestive system (Borovsky, D. [1988], supra).

Following the 1985 report, the isolated hormone, (a ten amino acid peptide) and two TMOF analogues were disclosed in U.S. Pat. Nos. 5,011,909 and 5,130,253, and in a 1990 publication (Borovsky, et al. [1990] *FASEB J.* 4:3015–3020). Additionally, U.S. Pat. No. 5,358,934 discloses truncated forms of the full length TMOF which have prolines removed from the carboxy terminus, including the peptides Tyr-Asp-Pro-Ala-Pro (SEQ ID NO. 25), Tyr-Asp-Pro-Ala-Pro-Pro (SEQ ID NO. 26), Tyr-Asp-Pro-Ala-Pro-Pro-Pro (SEQ ID NO. 27), and Tyr-Asp-Pro-Ala-Pro-Pro-Pro-Pro (SEQ ID NO. 28).

Neuropeptides Y (NPY) are an abundant family of peptides that are widely distributed in the central nervous system of vertebrates. NPY peptides have also been recently isolated and identified in a cestode, a turbellarian, and in terrestrial and marine molluscs (Maule et al., 1991 "Neuropeptide F: A Novel Parasitic Flatworm Regulatory Peptide from *Moniezia expansa* (Cestoda: Cyclophylidea)" *Parasitology* 102:309–316; Curry et al., 1992 "Neuropeptide F: Primary Structure from the Turbellarian, *Arthioposthia triangulata*" *Comp. Biochem. Physiol.* 101C:269–274; Leung et al., 1992 "The Primary Structure of Neuropeptide F (NPF) from the Garden Snail, *Helix aspersa*" *Regul. Pep.* 41:71–81; Rajpara et al., 1992 "Identification and Molecular Cloning of Neuropeptide Y Homolog that Produces Prolonged Inhibition in *Aplysia* Neurons" *Neuron.* 9:505–513).

Invertebrate NPYs are highly homologous to vertebrate NPYs. The major difference between vertebrate and invertebrate NPYs occurs at the C-terminus where the vertebrate NPY has an amidated tyrosine (Y) whereas invertebrates have an amidated phenylalanine (F). Because of this difference, the invertebrate peptides are referred to as NPF peptides.

Cytoimmunochemical analyses of NPY peptides suggest that they are concentrated in the brain of various insects, including the Colorado potato beetle *Leptinotarsa decemlineata* (Verhaert et al., 1985 "Distinct Localization of FMRFamide- and Bovine Pancreatic Polypeptide-Like Material in the Brain, Retrocerebal Complex and Subesophageal Ganglion of the Cockroach *Periplaneta americana*" L. Brain Res. 348:331–338; Veenstra et al., 1985 "Immunocytochemical Localization of Peptidergic Neurons and Neurosecretory Cells in the Neuro-Endocrine System of the Colorado Potato Beetle with Antisera to Vertebrate Regulatory Peptides" Histochemistry 82:9–18). Partial purification of NPY peptides in insects suggests that both NPY and NPF are synthesized in insects (Duve et al., 1981 "Isolation and Partial Characterization of Pancreatic Polypeptide-like Material in the Brain of the Blowfly *alliphora vomitoria*" Biochem. J. 197, 767–770).

Researchers have recently isolated two neuropeptides with NPF-like immunoreactivity from brain extracts of the Colorado potato beetle. The researchers purified the peptides using $C_{18}$ reversed phase high-pressure liquid chromatography (HPLC), and determined their structure using mass spectrometry. The deduced structures of these peptides are: Ala-Arg-Gly-Pro-Gln-Leu-Arg-Leu-Arg-Phe-amide (SEQ ID NO. 1) and Ala-Pro-Ser-Leu-Arg-Leu-Arg-Phe-amide (SEQ ID NO. 2) designated NPF I and NPF II, respectively (Spittaels, Kurt, Peter Verhaert, Chris Shaw, Richard N. Johnston et al. [1996] *Insect Biochem. Molec. Biol.* 26(4):375–382).

BRIEF SUMMARY OF THE INVENTION

The subject invention pertains to materials and methods for controlling pests. In a preferred embodiment, the subject invention involves the use of a polypeptide comprising an NPF peptide to control pests (referred to herein as the "NPF polypeptides"). Specifically exemplified are NPF polypeptides comprising an amino acid sequence selected from the group consisting of Ala-Arg-Gly-Pro-Gln-Leu-Arg-Leu-Arg-Phe-amide (SEQ ID NO. 1) and Ala-Pro-Ser-Leu-Arg-Leu-Arg-Phe-amide (SEQ ID NO. 2) and corresponding non-amidated NPF polypeptides Ala-Arg-Gly-Pro-Gln-Leu-Arg-Leu-Arg-Phe (SEQ ID NO. 3) and Ala-Pro-Ser-Leu-Arg-Leu-Arg-Phe (SEQ ID NO. 4), compositions comprising such NPF polypeptides and methods for using such compounds and pesticidal compositions. In a preferred mode, the NPF polypeptides comprise an amino acid sequence which consists of a native NPF peptide or a fragment, analogue, derivative or other functional equivalent of an NPF peptide.

Further exemplified NPF polypeptides include those comprising an amino acid sequence selected from the group consisting of Arg-Pro-Pro-Thr-Arg-Phe-Arg-Phe-amide (SEQ ID NO. 5), Arg-Pro-Pro-Thr-Arg-Phe-Arg-Phe (SEQ ID NO. 6), Ala-Pro-Gln-Leu-Arg-Leu-Arg-Phe-amide (SEQ ID NO. 7), Ala-Pro-Gln-Leu-Arg-Leu-Arg-Phe (SEQ ID NO. 8), Ala-Asn-Arg-Ser-Pro-Ser-Leu-Arg-Leu-Arg-Phe-amide (SEQ ID NO. 9), Ala-Asn-Arg-Ser-Pro-Ser-Leu-Arg-Leu-Arg-Phe (SEQ ID NO. 10), Ala-Asp-Arg-Ser-Pro-Ser-Leu-Arg-Leu-Arg-Phe-amide (SEQ ID NO. 11), Ala-Asp-Arg-Ser-Pro-Ser-Leu-Arg-Leu-Arg-Phe (SEQ ID NO. 12), Pro-Ile-Arg-Ser-Pro-Ser-Leu-Arg-Leu-Arg-Phe-amide (SEQ ID NO. 13), Pro-Ile-Arg-Ser-Pro-Ser-Leu-Arg-Leu-Arg-Phe (SEQ ID NO. 14), Ala-Gln-Arg-Ser-Pro-Ser-Leu-Arg-Leu-Arg-Phe-amide (SEQ ID NO. 15), Ala-Gln-Arg-Ser-Pro-Ser-Leu-Arg-Leu-Arg-Phe (SEQ ID NO. 16), Arg-Ser-Pro-Ser-Leu-Arg-Leu-Arg-Phe-amide (SEQ ID NO. 17), Arg-Ser-Pro-Ser-Leu-Arg-Leu-Arg-Phe (SEQ ID NO. 18), Pro-Ser-Leu-Arg-Leu-Arg-Phe-amide (SEQ ID NO. 19), Pro-Ser-Leu-Arg-Leu-Arg-Phe (SEQ ID NO. 20), Leu-Arg-Leu-Arg-Phe-amide (SEQ ID NO. 21), Leu-Arg-Leu-Arg-Phe (SEQ ID NO. 22), Arg-Pro-Pro-Thr (SEQ ID NO. 23), and Arg-Phe-Arg-Phe (SEQ ID NO. 24). NPF polypeptides of SEQ ID NOs. 5, 7, 9, 11, 13, and 15 are native NPF peptides from mosquito, American cockroach, or fruitfly, and are homologous with the amino acid sequences of SEQ ID NOs. 1 and 2, which are native to the Colorado potato beetle. NPF polypeptides of SEQ ID NOs. 6, 8, 10, 12, 14, and 16 are the respective non-amidated versions of these native NPF peptides. Specifically exemplified NPF analogues are those comprising an amino acid sequence selected from the group consisting of SEQ ID NOs. 17–24.

The NPF polypeptides of the subject invention are particularly active against blood-ingesting pests, e.g., species of mosquitoes such as *Aedes aegypti*, which are vectors of many arthropod-borne viral diseases (arboviruses). These pests utilize serine esterases, such as TTLE as their primary blood digesting enzymes.

One aspect of the subject invention pertains to methods for controlling blood-ingesting pests by applying to a pest or to a pest-inhabited locus, a pesticidal formulation comprising (a) an NPF polypeptide comprising a native NPF peptide or functional equivalent thereof and (b) a pesticidally effective carrier.

The subject invention further pertains to the use of NPF polypeptides to control other pests, including non-blood ingesting agricultural pests. These pests include, for example, coleopterans (beetles), lepidopterans (caterpillars), and mites. The compounds of the subject invention can also be used to control household pests including, but not limited to, ants and cockroaches.

The present invention also includes addition salts, complexes and prodrugs such as esters of the NPF polypeptides, especially the nontoxic pharmaceutically or agriculturally acceptable acid addition salts. The acid addition salts can be prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. Also, the N-terminus and C-terminus of the NPF polypeptides can be chemically modified to further inhibit proteolysis by metabolic enzymes, for example, by N-terminal carboxylation and/or C-terminal amidation.

Dextrorotory amino acids can also be usefully employed in the NPF polypeptides of the present invention to inhibit the ability of proteases to degrade the peptides of the subject invention.

NPF polypeptides in which only conservative substitutions have been made are also provided by the present invention. Analogues of the NPF polypeptides which have one or more amino acid substitutions forming a branched peptide (e.g., by substitution with an amino acid or amino acid analogue having a free amino- or carboy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally, to provide a sulfhydryl group for disulfide bond formation), are also provided.

Also, derivation of the NPF polypeptides with long chain hydrocarbons facilitates passage through the cuticle into the pest body cavity. Therefore, a further embodiment of the subject invention pertains to compositions comprising the NPF polypeptides bound to lipids or other carriers.

Analogues and derivatives, and other functional equivalents, included within the scope of the invention are those which retain some or all of the pesticidal activity of native NPF peptides, or those which show improved activity as compared to a corresponding native NPF peptide. Thus, included within the scope of the invention are pesticidally active native NPF peptides, fragments, analogues (e.g., homologues), derivatives, or other functional equivalents of native NPF peptides.

Yet another aspect of the subject invention pertains to DNA sequences encoding the peptides of the subject invention disclosed herein. These DNA sequences can be readily synthesized by a person skilled in the art. The sequences may be used to transform an appropriate host to confer upon that host the ability to express the NPF polypeptides. Hosts of particular interest include bacteria, algae, yeasts, insect viruses, and plants. For each of these hosts, the DNA sequences may be specifically designed by a person skilled in the art to utilize codons known to be optimally expressed in the particular hosts. Advantageous promoters can also easily be utilized. Bacteria, yeasts, plants, algae, viruses, and other hosts each may be used to produce peptide for further use, or these hosts can be used as vehicles for direct application of the peptide to the target pest. A plant species can be transformed to express the NPF polypeptides, resulting in a plant variety that is toxic to a target pest species which feeds on the plant. Pest control is achieved when the pest ingests the transformed plant material thereby exposing the pest to the NPF polypeptide. Methods for transforming plant cells utilizing, for example *Agrobacteria*, are well known to those skilled in the art.

Another aspect of the subject invention pertains to a method of controlling pests comprising administering to said pest an effective amount of one or more NPF polypeptides.

The subject invention provides pest control compositions wherein the NPF polypeptides are formulated for application to the target pests or their situs. In a specific embodiment, the present invention provides recombinant hosts, which express an NPF polypeptide. The recombinant host can be a procaryotic or eucaryotic cell, including for example, yeast or algae cells which are transformed to express an NPF polypeptide. The transformed host may also be a virus. The transformed host can be applied to a pest's habitat, (e.g., where the target pest is a mosquito, the transformed host can be applied to a body of water which serves as a habitat for mosquito larvae), where the pest will ingest the transformed host resulting in control of the pest by the NPF polypeptide.

The methods and materials of the subject invention provide a novel approach to controlling pests and pest-transmitted diseases.

As used herein, the term "pesticidally effective" is used to indicate an amount or concentration of a pesticide, e.g., an NPF polypeptide, which is sufficient to reduce the number of pests in a geographical locus, as compared to a corresponding geographical locus in the absence of the amount or concentration of the pesticide.

The term "pesticidal" is not intended to refer only to the ability to kill pests, but also includes the ability to interfere with a pest's life cycle in any way that results in an overall reduction in the pest population. For example, the term "pesticidal" includes inhibition or elimination of reproductive ability of a pest, as well as inhibition of a pest from progressing from one form to a more mature form, e.g., transition between various larval instars or transition from larvae to pupa or pupa to adult. Further, the term "pesticidal" is intended to refer to all phases of a pest life cycle; thus, for example, the term includes larvicidal, ovicidal and adulticidal action.

The word "transform" is broadly used herein to refer to introduction of an exogenous polynucleotide sequence into a prokaryotic or eukaryotic cell by any means known in the art (including for example, direct transmission of a polynucleotide sequence from a cell or virus particle, transmission by infective virus particles, and transmission by any known polynucleotide-bearing substance) resulting in a permanent or temporary alteration of genotype and in an immortal or non-immortal cell line.

The terms "peptide," "polypeptide," and "protein" as used herein are intended to refer to amino acid sequences of any length.

Without intending to be bound by theory, the current invention is based on the determination that NPF adversely affects TTLE biosynthesis in the midgut of female *Aedes aegypti* fed a blood meal and injected with NPF polypeptide. Because the structure of NPF is different from TMOF it appears that NPF does not bind to a TMOF-specific binding site on the gut receptor but to a different site on the same or different receptor. Furthermore, cytoimmunochemical analysis, by the inventors, of the mosquito gut after the blood meal, using antiserum against NPF, has surprisingly revealed exocrine cells with NPF-like molecules that are synthesized by mosquito epithelial cells 24 hours after a blood meal. NPF therefore appears to be a secondary signal in a cascade of signals: first TMOF is released from the ovary, TMOF then binds to a TMOF gut receptor (Borovsky et al. [1994] *FASEB J.* 8:350–355) that stimulates the synthesis and release of NPF from gut specific exocrine cells. NPF then binds to a receptor site on the gut at a site which may be adjacent to or part of the TMOF receptor, resulting cessation of biosynthesis of TTLE. This surprising discovery opens the door to a new generation of NPF pesticides, which inhibit biosynthesis of TTLE in a more direct manner than previously disclosed TMOF peptides.

BRIEF DESCRIPTION OF THE SEQUENCES

SEQ ID NO. 1 is an amidated neuropeptide designated NPF I.

SEQ ID NO. 2 is an amidated neuropeptide designated NPF II.

SEQ ID NO. 3 is a non-amidated version of the NPF I peptide.

SEQ ID NO. 4 is a non-amidated version of the NPF II peptide.

SEQ ID NOs. 5–24 are amidated and non-amidated versions of NPF polypeptides.

SEQ ID NOs. 25–28 are TMOF peptides.

DETAILED DISCLOSURE OF THE INVENTION

Figure 1:
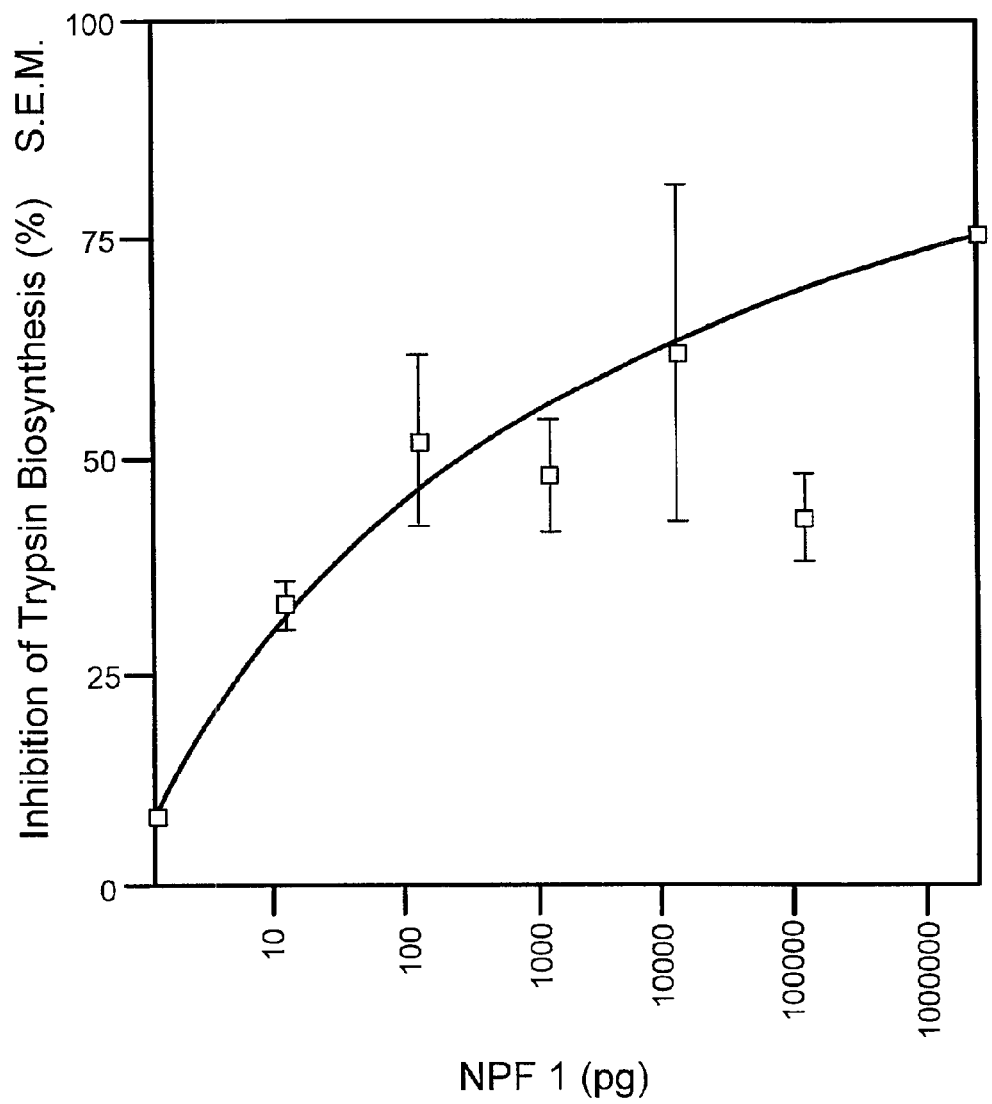
FIG. 1 is a graph showing the inhibitory affect of NPF I on trypsin biosynthesis when injected into whole mosquitos. NPF I resulted in a 50% inhibition of trypsin biosynthesis when injected at a $1 \times 10^{-6}$ M concentration.

The subject invention concerns NPF polypeptides that can be used to control target pests. Specifically exemplified is the use of NPF polypeptides in controlling mosquitos and other pests. A method of controlling pests is also specifically exemplified herein, which method employs the use of NPF I and/or NPF II, which have the sequences Ala-Arg-Gly-Pro-Gln-Leu-Arg-Leu-Arg-Phe-amide (SEQ ID NO. 1) and Ala-Pro-Ser-Leu-Arg-Leu-Arg-Phe-amide (SEQ ID NO. 2), respectively, as well as non-amidated versions of NPF I and NPF II, Ala-Arg-Gly-Pro-Gln-Leu-Arg-Leu-Arg-Phe (SEQ ID NO. 3) and Ala-Pro-Ser-Leu-Arg-Leu-Arg-Phe (SEQ ID NO. 4), respectively.

Further exemplified NPF polypeptides include those comprising an amino acid sequence selected from the group consisting of Arg-Pro-Pro-Thr-Arg-Phe-Arg-Phe-amide (SEQ ID NO. 5), Arg-Pro-Pro-Thr-Arg-Phe-Arg-Phe (SEQ ID NO. 6), Ala-Pro-Gln-Leu-Arg-Leu-Arg-Phe-amide (SEQ ID NO. 7), Ala-Pro-Gln-Leu-Arg-Leu-Arg-Phe (SEQ ID NO. 8), Ala-Asn-Arg-Ser-Pro-Ser-Leu-Arg-Leu-Arg-Phe-amide (SEQ ID NO. 9), Ala-Asn-Arg-Ser-Pro-Ser-Leu-Arg-Leu-Arg-Phe (SEQ ID NO. 10), Ala-Asp-Arg-Ser-Pro-Ser-Leu-Arg-Leu-Arg-Phe-amide (SEQ ID NO. 11), Ala-Asp-Arg-Ser-Pro-Ser-Leu-Arg-Leu-Arg-Phe (SEQ ID NO. 12), Pro-Ile-Arg-Ser-Pro-Ser-Leu-Arg-Leu-Arg-Phe-amide (SEQ ID NO. 13), Pro-Ile-Arg-Ser-Pro-Ser-Leu-Arg-Leu-Arg-Phe (SEQ ID NO. 14), Ala-Gln-Arg-Ser-Pro-Ser-Leu-Arg-Leu-Arg-Phe-amide (SEQ ID NO. 15), Ala-Gln-Arg-Ser-Pro-Ser-Leu-Arg-Leu-Arg-Phe (SEQ ID NO. 16), Arg-Ser-Pro-Ser-Leu-Arg-Leu-Arg-Phe-amide (SEQ ID NO. 17), Arg-Ser-Pro-Ser-Leu-Arg-Leu-Arg-Phe (SEQ ID NO. 18), Pro-Ser-Leu-Arg-Leu-Arg-Phe-amide (SEQ ID NO. 19), Pro-Ser-Leu-Arg-Leu-Arg-Phe (SEQ ID NO. 20), Leu-Arg-Leu-Arg-Phe-amide (SEQ ID NO. 21), Leu-Arg-Leu-Arg-Phe (SEQ ID NO. 22), Arg-Pro-Pro-Thr (SEQ ID NO. 23), and Arg-Phe-Arg-Phe (SEQ ID NO. 24). NPF polypeptides of SEQ ID NOs. 5, 7, 9, 11, 13, and 15 are native NPF peptides from mosquito, American cockroach, or fruitfly, and exhibit homology with the amino acid sequences of SEQ ID NOs. 1 and 2, which are native to the Colorado potato beetle. NPF polypeptides of SEQ ID NOs. 6, 8, 10, 12, 14, and 16 are the respective non-amidated versions of these native NPF peptides. Specifically exemplified NPF analogues are those comprising an amino acid sequence selected from the group consisting of SEQ ID NOs. 17–24.

The term "pest" as used herein includes mosquitoes, insects and other organisms which adversely affect, humans, plants or animals, including, for example, organisms that remove blood, tissue and/or any other fluid from their prey or host. Pests controlled according to the subject invention specifically include those which regulate TTLE concentrations in the gut by a mechanism which involves the binding of a ligand to a receptor to trigger an increase or a decrease in the synthesis of digestive enzymes, e.g., TMOF binding to its receptor. Examples of pests which can be controlled according to the subject invention include, but are not limited to, mosquitos, fleshflies, fleas, sandflies, houseflies, dogflies, and insects which attack plants.

The pest control compositions according to the subject invention comprise an NPF polypeptide, or a fragment, derivative, analogue or other functional equivalent of an NPF polypeptide, as a component, or as the sole component. The pest control compositions may further comprise a carrier solution, compound, or molecule. Pest control compositions of the subject invention also include an NPF polypeptide, or a fragment, derivative, analogue or other functional equivalent of an NPF polypeptide, contained in or associated with a cell, virus, plant, or membrane. Examples include, but are not limited to, transformed bacteria, mammalian cells, algae, fungi, yeast viruses, or plants that produce an NPF polypeptide.

The term "functional equivalent" as used herein refers to a polypeptide sequence comprising full-length native NPF polypeptide, or a comprising fragment, analogue (e.g., homologue), or derivative of a full-length native NPF. Functional equivalents include, for example, an NPF polypeptide in salt, complex, analogue, or derivative form as well as a fragment, derivative or analogue of a native NPF peptide, which retains some or all of the biological activity of the native NPF peptide.

The NPF polypeptides may be presented as fusion proteins or peptides, the amino acid sequence of which includes one or more NPF polypeptides of the present invention. In various specific embodiments, two or more of the NPF polypeptides are linked, for example, by peptide bonds between the N-terminus of one portion and the C-terminus of another portion. In other aspects, one or more of the NPF polypeptides can be linked to one or more heterologous polypeptides to form pesticidal fusion peptides. Molecules comprising such portions linked by hydrocarbon linkages are also provided. Derivatives of the foregoing fusion proteins are also provided (e.g., branched, curcularized, N-terminal carboxylated or C-terminal amidated).

In one embodiment the fusion protein or peptide comprises a repeating unit of at least 4 amino acids (e.g., a multimer). There may be, for example, from 2 to 10 or more repeating units. Preferably, the repeating unit is connected through at least one amino acid which is cleaved by a pest gut enzyme. Methods of recombinantly producing peptides in cells as multimers are known in the art. (Rao et al., 1996 "Synthesis and expression of genes encoding putative insect neuropeptide precursors in tobacco," Gene 175:1–5; Tortiglione et al., 1999 "New Genes for Pest Control," Genetics and Breeding for Crop Quality and Resistance, 159–163). For example, a tandemly repeated DNA cassette for the expression of NPF peptides can be constructed. As used herein, a pest gut enzyme is an enzyme which is present in the gut of a pest. Preferably, the pest is a mosquito or a lepidopteran. In a specific embodiment, the repeating units are connected through an arginine.

Analogues which have one or more amino acid substitutions forming a branched peptide (e.g., by substitution with an amino acid or amino acid analogue having a free amino- or carboxy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally, to provide a sulfhydryl group for disulfide bond formation), are also provided.

Nonclassical amino acids or chemical amino acid analogues can replace existing amino acid residues of the NPF polypeptides or be inserted into the NPF polypeptides between existing amino acid residues of the NPF polypeptides or added to a terminus of the NPF polypeptides of the present invention. Non-classical amino acids include, but are not limited to, the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Furthermore, the amino acid can be D (dextrorotary) or L (levorotary). Dextrorotary amino acids are indicated herein by a parenthetical D, i.e., "(D)", immediately preceding the dextrorotary amino acid.

The NPF compounds include peptides containing, as a primary amino acid sequence, all or part of an exemplified NPF polypeptide sequence. The NPF compounds thus include NPF polypeptides having conservative substitutions, i.e., altered sequences in which functionally equivalent amino acid residues are substituted for residues within the sequence resulting in a peptide which is functionally active. For example, one or more amino acid residues within the sequence can be substituted by another amino acid of a similar polarity which acts as a functional equivalent, resulting in a silent alteration. In one aspect of the present invention, conservative substitutions for an amino acid within the sequence may be selected from other members of the class to which the amino acid belongs (see Table 1). Conservative substitutions also include substitutions by amino acids having chemically modified side chains which do not eliminate the pesticidal properties of the resulting NPF compound.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In a specific embodiment, the subject invention is directed toward a method of controlling blood-ingesting pests comprising preparing a treatment comprising an NPF compound and applying said treatment to said blood-ingesting pests. In another embodiment these peptides are used to control agricultural pests.

Preparation of novel pest control compounds. The NPF polypeptides of the invention can be prepared by well-known synthetic procedures. For example, the polypeptides can be prepared by the well-known Merrifield solid support method. See Merrifield (1963) J. Amer. Chem. Soc. 85:2149–2154 and Merrifield (1965) Science 150:178–185. This procedure, using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations since removal of the excess reagents at each step is effected simply by washing of the polymer.

Alternatively, these peptides can be prepared by use of well-known molecular biology procedures. Polynucleotides, such as DNA sequences, encoding the NPF polypeptides of the invention can be readily synthesized. Such polynucleotides are a further aspect of the present invention. These polynucleotides can be used to genetically engineer eukaryotic or prokaryotic cells, for example, bacteria cells, insect cells, algae cells, plant cells, mammalian cells, yeast cells or fungi cells for synthesis of the peptides of the invention. Viruses may also be genetically modified using such polynucleotides, to serve as vectors for the delivery of the polynucleotides to insect pests or to other cells. One example of a cell line usefully transformed according to the teachings of the present invention is the insect cell line Sf9 (Spodoptera frugiperda), deposit number ATCC CRL 1711, available from the American Type Culture Collection, 12301 Parklawn Drive, Rockville, Md. 20852 USA. An example of a useful virus includes the Baculovirus, Autographa californica Nuclear Polyhedrosis Virus (AcNPV), which is available from Texas A&M University, Texas Agricultural Experiment Station, College Station, Tex. 77843, and described in Smithand Summers (1978) Virology 89:517–527; and (1979) J. Virology 30:828–838. Other nuclear polyhedrosis viruses (See World Health Organization Technical Report No. 531) such as Spodoptera frugiperda (Sf MNPV), Choristoneura fumiferana (Cf MNPV) (Smithand Summers [1981] J. Virol. 39:125–137), or Spodoptera littoralis (S1 NPV) (Harrap, et al. [1977] Virology 79:14–31) can be used instead of Autographa californica NPV. Other insect cell lines can also be substituted for Spodoptera frugiperda (Sf9), for example, Trichoplusia ni (Volkman and Summers [1975] J. Virol. 16:1630–1637), Spodoptera exigua, Choristoneura fumiferana (Smith, and Summers [1981] J. Virol. 39:125–137) and Spodoptera littoralis (Harrap, K. A. et al. [1977] Virology 79:14–31).

In yet another embodiment, the subject invention is directed to polynucleotides which encode the subject NPF polypeptides. Polynucleotides can be produced by routine methods known in the art. [See S. L. Beaucage and M. H. Caruthers (1981), *Tetrahedran Lett*. 22:1859].

The polynucleotides of the present invention can be amplified using Polymerase Chain Reaction (PCR), a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, et al. [1985] "Enzymatic Amplification of β-Globin Genomic Sequences and Restriction Site Analysis for Diagnosis of Sickle Cell Anemia," *Science* 230:1350–1354.). PCR employs the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template another primer, each cycle essentially doubles the amount of DNA fragment produced in the previous cycle, resulting in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other useful enzymes are known to those skilled in the art.

PCR primers can be designed from the DNA sequences of the subject invention. In performing PCR amplification, a certain degree of mismatch can be tolerated between primer and template. Therefore, mutations, deletions, and insertions (especially additions of nucleotides to the 5' end) of the exemplified sequences fall within the scope of the subject invention. These PCR primers can be used to amplify genes of interest from a sample providing another method for identifying and characterizing polynucleotide sequences encoding the NPF polypeptides.

The various methods employed in the preparation of the plasmids and transformation of host organisms are well known in the art and are described, for example, in U.S. Pat. Nos. 5,011,909 and 5,130,253. These patents are incorporated herein by reference. These procedures are also described in Maniatis, et al. (1982) *Molecular Cloning: A Laboratory Manual*, Cold Spring Harbor Laboratory, New York. Thus, it is within the skill of those in the genetic engineering art to extract DNA from its source, perform restrictions enzyme digestions, electrophorese DNA fragments, tail and anneal plasmid and insert DNA, ligate DNA, transform cells, e.g., *E. coli* or plant cells, prepare plasmid DNA, electrophorese proteins, and sequence DNA.

Production of recombinant hosts. In another embodiment, the subject invention is directed to a cell transformed with a polynucleotide encoding a pesticidal NPF polypeptide. Hosts, which may be employed according to techniques well known in the art for the production of the NPF polypeptides of the present invention, include unicellular microorganisms, such as prokaryotes, i.e., bacteria; and eukaryotes, such as fungi, (including yeasts), algae, protozoa, molds, and the like, as well as plant cells, both in culture or in planta, and animal cells. Specific bacteria which are susceptible to transformation include members of the Enterobacteriaceae, such as strains of *Escherichia coli; Salmonella; Bacillaceae*, such as *Bacillus subtilis; Pseudomonas; Pneumococcus; Streptococcus; Haemophilus influenzae*, and yeasts such as *Saccharomyces*, among others.

In one embodiment of the present invention, the transformed host is *Bacillus sphaericus*, which is known to be highly specific for control of mosquito larvae. In a preferred embodiment, the host is *Bacillus sphaericus*, serotype H5a5b, available from Abbott Laboratories as VectoLex CG Biological Larvicide (EPA Reg. No. 275-77).

The polynucleotide sequences of the subject invention can be introduced directly into the genome of the transformable host cell or can first be incorporated into a vector which is then introduced into the host. Exemplary methods of incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids, and phages.

It is well known in the art that when synthesizing a gene for improved expression in a host cell it is desirable to design the gene such that its frequency of codon usage approaches the frequency of preferred codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell.

Thus, in one embodiment of the subject invention, bacteria, algae, fungi, yeast, plants, or other cells can be genetically engineered, e.g., transformed with polynucleotides encoding the subject peptides to attain desired expression levels of the subject peptides. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for the host cell, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed genes in the host cell to specify that amino acid. As is appreciated by those skilled in the art, the distribution frequency of codon usage utilized in the synthetic gene is a determinant of the level of expression.

Assembly of the polynucleotide sequences of this invention can be performed using standard technology known in the art. For example, a structural gene designed for enhanced expression in a host cell can be assembled within a DNA vector from chemically synthesized oligonucleotide duplex segments. Preferably, the DNA vector or construct has an operable promoter and suitable termination signals. The polynucleotide sequence can be introduced into a host cell and expressed by means known in the art. Preferably, the NPF compound produced upon expression of the nucleotide sequence is functionally equivalent to the corresponding purified NPF polypeptide. The present invention also comprises expression cassettes comprising the polynucleotides of the present invention and a expression vectors comprising polynucleotides and/or expression cassettes of the present invention. According to the subject invention, "functionally equivalent" indicates retention of function such as, for example, pest control activity.

The present invention also includes chimeric polypeptides comprising one or more heterologous polypeptides joined to one or more NPF polypeptides, and also includes chimeric polypeptides comprising two or more NPF polypeptides joined together. The portions which are combined need not, themselves, be pesticidal so long as the combination of portions creates a chimeric protein which is pesticidal. The chimeric toxins may include portions from toxins which do not necessarily act upon the TMOF receptor including, for example, toxins from *Bacillus thuringiensis* (*B.t.*). *B.t.* toxins and their various toxin domains are well known to those skilled in the art. Preferred toxins originate with various strains of *B.t.* including, for example, *B.t. israeliensis, B.t. tenebrionis, B.t. san diego, B.t. aizawai, B.t. subtoxicus, B.t. alesti, B.t. gallaeriae, B.t. sotto, B.t. kurstaki, B.t. berliner, B.t. tolworthi, B.t. dendrolimus* and *B.t. thuringiensis*, and other *B.t.* toxins known in the art such as the various delta-endotoxins described in U.S. Pat. No. 5,686,069.

With the teachings provided herein, one skilled in the art can readily produce and use the various compounds and polynucleotide sequences described herein.

The polynucleotide sequences and compounds useful according to the subject invention include not only the exemplified sequences but also fragments of these sequences, variants, mutants, and fusion proteins which retain the characteristic pesticidal activity of the peptides specifically exemplified herein. As used herein, the terms "variants" or "variations" of genes refer to polynucleotides having different nucleotide sequences but encoding the same polypeptides or encoding equivalent peptides having pesticidal activity. As used herein, the term "equivalent" in reference to a peptide or polypeptide refers to compounds exhibiting some or all of the biological activity of native NPF peptides.

Variations of genes may be readily constructed using standard techniques for making point mutations. Also, fragments of these genes can be made using commercially available exonucleases or endonucleases according to standard procedures. For example, enzymes such as the nuclease, BAL31, or site-directed mutagenesis can be used to systematically excise nucleotides from the ends of the genes. Also, genes which encode active fragments may be obtained using a variety of restriction enzymes. Proteases may be used to directly obtain active fragments of these peptides.

Polynucleotide sequences encoding NPF polypeptides can be introduced into a wide variety of microbial or plant hosts with the result that expression of the gene results, directly or indirectly, in the production and maintenance of the NPF polypeptides. With suitable microbial hosts, e.g., yeast, *Chlorella*, the microbes can be applied to the situs of the pest, where they will proliferate and be ingested by pest organisms, resulting in control of the pest. Alternatively, the microbe hosting the gene can be killed and may optionally be treated under conditions that prolong the activity of the toxin and stabilize the cell. Such killed cells can be applied to the habitat and/or to the host or prey of the target pest. In one embodiment, the microbial or other host is transformed such that the gene encoding the pesticidal NPF polypeptide is only exressed or maintained for a relatively short period of time, such as days or weeks, so that the expression of the NPF polypeptide does not continue indefinitely.

A wide variety of methods are available for introducing a polynucleotide sequence encoding a pesticidal polypeptide into a microorganism host under conditions which allow for stable maintenance and expression of the gene. These methods are well known to those skilled in the art and include, for example, the methods described in U.S. Pat. No. 5,135,867, which is incorporated herein by reference.

Synthetic genes which encode peptides which are functionally equivalent to the NPF polypeptide of the subject invention can also be used to transform hosts. Methods for the production of synthetic genes can be found in, for example, U.S. Pat. No. 5,380,831.

Recombinant cells expressing a pest control compound can be treated to prolong the pesticidal activity of the NPF polypeptide and stabilize the cell. For example, such cells can be formulated as a pesticide microcapsule comprising the NPF polypeptide within a stabilized cellular structure that protects the toxin when the microcapsule is applied to the environment of the target pest. Suitable host cells include prokaryotes and eukaryotes. Preferred hosts include prokaryotes and lower eukaryotes, such as algae and fungi. The recombinant cell will preferably be intact and be substantially in the proliferative form when treated, rather than in a spore form.

Treatment of the microbial cell, e.g., a microbe containing the polynucleotide sequence encoding the pesticidal polypeptide, can be by chemical or physical means, or by a combination of chemical and/or physical means, so long as the technique does not completely diminish the properties of the toxin, nor diminish the cellular capability of protecting the toxin. Methods for treatment of microbial cells are disclosed in U.S. Pat. Nos. 4,695,455 and 4,695,462, which are incorporated herein by reference.

Methods and formulations for control of pests. Control of pests using the NPF polypeptides of the subject invention can be accomplished by a variety of methods known to those skilled in the art. These methods include, for example, the application of recombinant microbes to the pests (or their locations), and the transformation of plants with genes (polynucleotide sequences) encoding the NPF polypeptides of the subject invention. Transformations can be made by those skilled in the art using standard techniques. Materials necessary for these transformations are disclosed herein or are otherwise readily available to the skilled artisan.

The plant pests which can be controlled by the compounds of the subject invention generally belong to the phylum Arthropoda, including pests of the orders Coleoptera, Lepidoptera, Hemiptera and Thysanoptera. Other pests which can be controlled according to the subject invention include members of the orders Diptera, Siphonaptera, Hymenoptera and Phthiraptera. Pests of the class Arachnida, such as ticks, mites, and spiders, can also be controlled by the NPF polypeptides of the present invention.

The use of the compounds of the subject invention to control pests can be accomplished readily by those skilled in the art having the benefit of the instant disclosure. For example, the control compounds may be encapsulated, included in a granular form, solubilized in water or other appropriate solvent, powdered, and included into any appropriate formulation for direct application to the pest. In a preferred embodiment for the control of plant pests, plants may be genetically transformed to express the pest control compound such that a pest feeding upon the plant will ingest the control compound and thereby be controlled.

Where the polynucleotide sequence is introduced via a suitable vector into a microbial host, and said host is applied to the environment in a living state, it is preferred that certain host microbes be used. Microorganism hosts are selected which are known to occupy the "phytosphere" (phylloplane, phyllosphere, rhizosphere, and/or rhizoplane) of one or more crops of interest or the situs where the pest proliferates. These microorganisms are selected so as to be capable of successfully competing in the particular environment (crop and other insect habitats) with the wild-type organisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Preferred microorganisms include bacteria, e.g., genera *Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes*; fungi, particularly yeast, e.g., genera *Saccharomyces, Cryptococcus, Kluyveromyces, Sporobolomyces, Rhodotorula,* and *Aureobasidium*; and algae, e.g., *Chlorella*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii* and *Bacillus thurnigensis*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Pigmented microorganisms are particularly preferred.

Formulated bait granules containing an attractant and the NPF polypeptides, or recombinant microbes comprising toxin-encoding polynucleotide sequences, can be applied to the soil. Formulated product can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the concentration of NPF polypeptide in the pesticidal formulations of the present invention will vary widely depending upon the nature of the particular formulation, particularly whether it is a concentrate or to be used directly, and on the potency of the NPF polypeptide(s) selected. The NPF polypeptide will be present in at least about 0.0001% by weight and may be 100% by weight. The dry formulations will have from about 0.0001–95% by weight of the NPF polypeptide, while the liquid formulations will generally be from about 0.0001–60% by weight of the solids in the liquid phase. The formulations that contain cells will generally have from about 1 to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like, and/or to hosts or prey of the pests, e.g., plants, and humans or other animals.

In applications to the environment of the target pest, a transformant strain can be applied to the natural habitat of the pest. In some cases, the transformant strain will continue to grow in the pest upon ingestion and produce NPF polypeptide following ingestion by the pest. The transformed organism may be applied by spraying, soaking, injection into the soil, seed coating, seedling coating or spraying, or the like. Where administered in the environment, concentrations of the organism will generally be from 1 to $10^{10}$ cells/ml, and the volume applied per hectare will be generally from about 0.1 oz to 2 lbs or more. Where administered to a plant part inhabited by the target pest, the concentration of the organism will usually be from $10^3$ to $10^6$ cells/cm².

In aquatic environments, pest control may be attained at or below the surface by adjusting the specific gravity of the microbe. This can be accomplished by, for example, varying the lipid content of the transformant microorganism strain. It is known that indigenous aquatic algae float due to their lipid content. A variation in lipid content will allow the transformant strain to be distributed at desired depths below the water surface.

For commercial formulations, the organisms may be maintained in a nutrient medium which maintains selectivity and results in a low rate of proliferation. Various media may be used, such as yeast extract or L-broth. Once the organism is to be used in the field, the non-proliferating concentrate may be introduced into an appropriate selective nutrient medium, grown to high concentration, generally from about $10^5$ to $10^9$ cells/ml and may then be employed for introduction into the environment of the pest.

All of the U.S. patents and other references cited herein are hereby incorporated by reference, as are U.S. patent application Ser. No. 09/295,846, (UF-223) "Transformed Cells Useful for the Control of Pests"; U.S. patent application Ser. No. 09/551,737, (UF-223C1) "Transformed Cells Useful for the Control of Pests"; U.S. patent application Ser. No. 09/296,113, (UF-224) "Materials and Methods Useful for the Control of Insect Larvae"; U.S. patent application Ser. No. 09/551,738, (UF-224C1) "Materials and Methods Useful for the Control of Insect Larvae"; U.S. patent application Ser. No. 09/295,996, (UF-230) "Novel Peptides and the Use Thereof to Control Pests"; and U.S. patent application Ser. No. 09/295,924, "Compositions and Methods for Controlling Pests".

Following are examples which illustrate procedures for practicing the invention. These examples should not be construed as limiting. All percentages are by weight and all solvent mixture proportions are by volume unless otherwise noted.

EXAMPLE 1

Effect of NPF Polypeptides on Trypsin Biosynthesis

Figure 2:
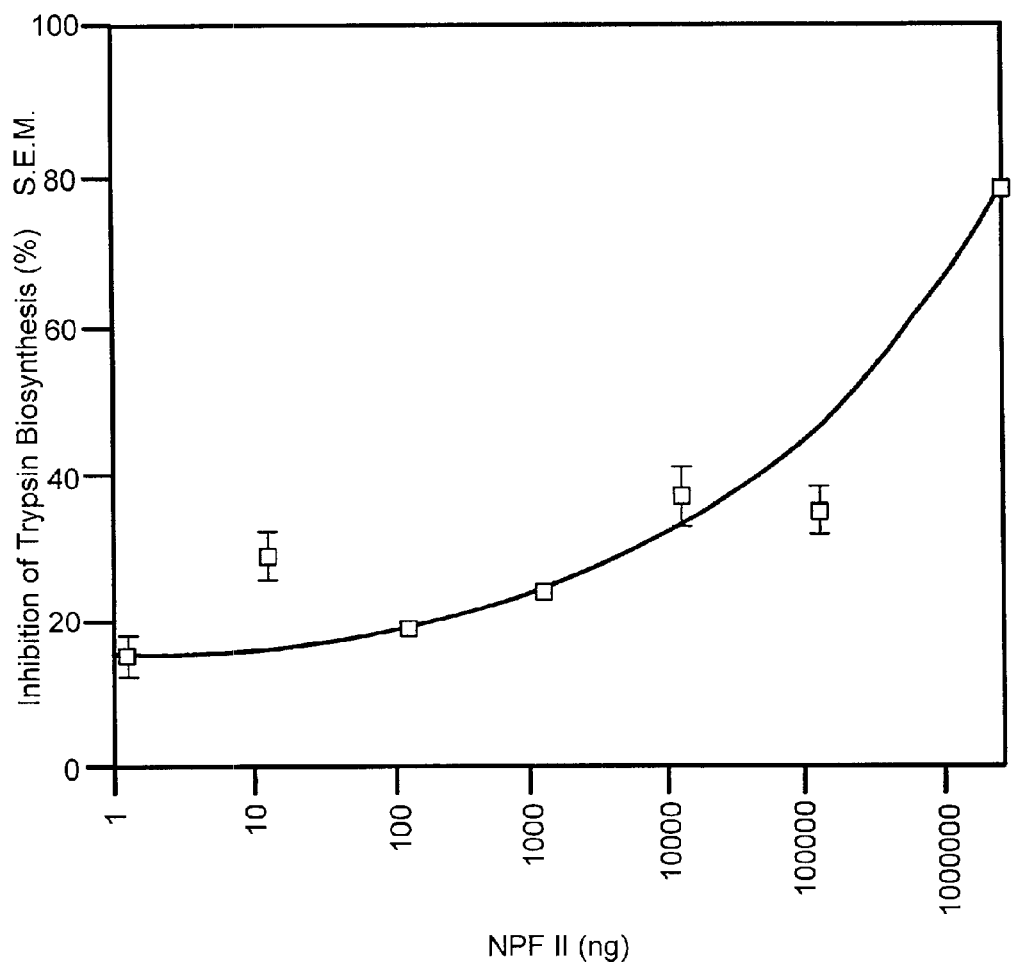
FIG. 2 is a graph showing the inhibitory affect of NPF II on trypsin biosynthesis when injected into whole mosquitos. NPF II resulted in a 35% inhibition of trypsin biosynthesis at a $1 \times 10^{-3}$ M concentration.
Figure 3:
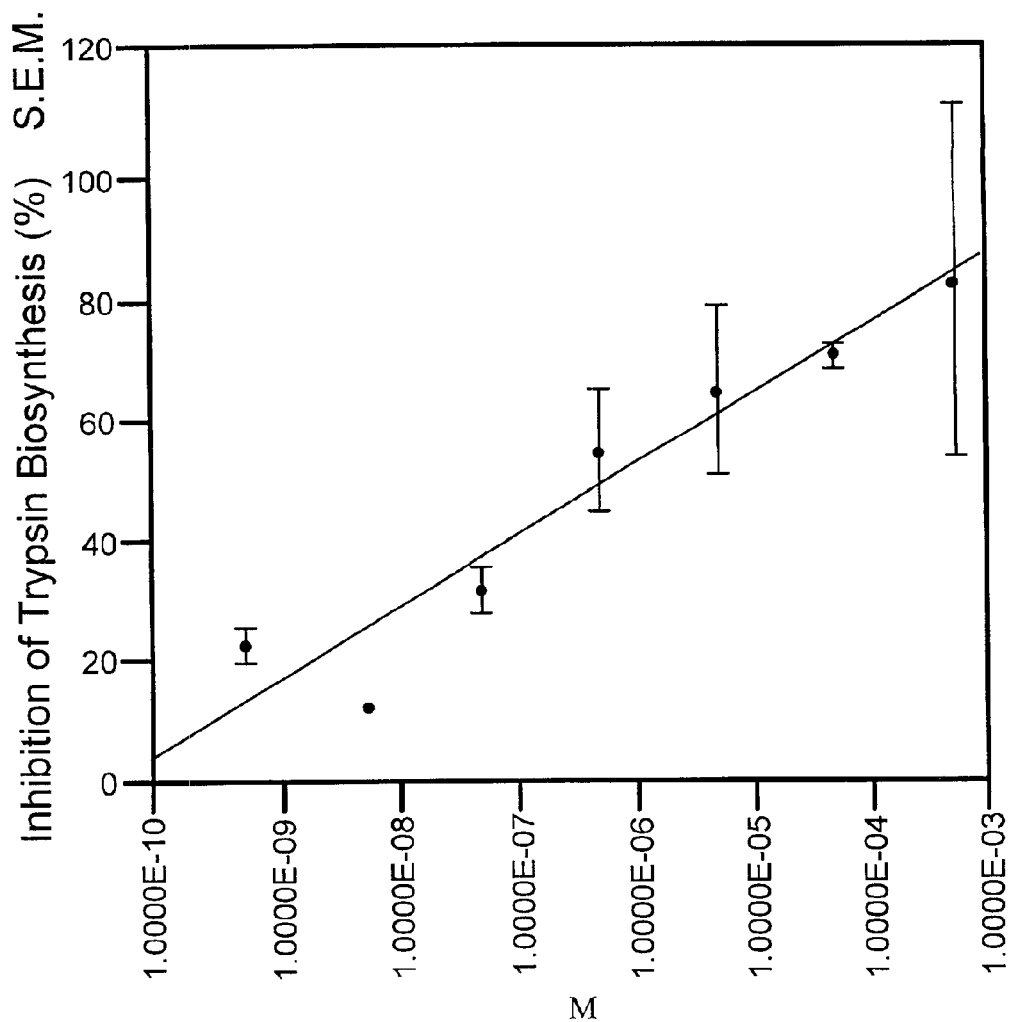
FIG. 3 is a graph showing the inhibitory affect of NPF I on trypsin biosynthesis when injected into ligated mosquito abdomens. NPF I resulted in a 54% inhibition of trypsin biosynthesis at a $1 \times 10^{-6}$ M concentration. These results strongly suggest that NPF acts on a receptor in the gut and not through a cell signaling transduction pathway which originates in the brain.

To find out if NPF I and II affect trypsin biosynthesis in the midgut of female *Aedes aegypti*, females were fed a blood meal and immediately injected with 0.25 µl of the peptide at concentrations of 2.5 µg to 12.5 pg and 30 hours later the midguts were removed and assayed for trypsin biosynthesis (Borovsky et al., 1990 "Mosquito Oostatic Factor: A Novel Decapeptide Modulating Trypsin-Like Enzyme Biosynthesis in the Midgut" FASEB J. 4:3015–3020; Borovsky et al 1993 "Mass Spectrometry and Characterization of *Aedes aegypti* Trypsin Modulating Oostatic Factor (TMOF) and its Analog" Insect Biochem. Molec. Biol. 23:703–712). Each experiment was repeated 3 times (5 females per group) and the results are expressed as % inhibition of trypsin biosynthesis±S.E.M. (FIG. 1). Fifty percent inhibition of trypsin biosynthesis was achieved at a concentration of $10^{-6}$M NPF I. NPF II was effective at a dose of $10^{-3}$M (78%±10), at $10^{-6}$M NPF II inhibited trypsin biosynthesis by 35% (FIG. 2).

To determine if NPF I releases a neuroendocrine factor from the brain or the thoracic ganglia which in turn may release TMOF from the ovary, female *Aedes aegypti* were fed a blood meal, immediately ligated and injected with different concentrations of NPF I($10^{-3}$M to $10^{-9}$M) in 0.25 $\mu$l of sterile distilled water. Thirty hours later, abdomens were removed and 3 groups of 5 abdomens per NPF concentration were assayed for trypsin biosynthesis (Borovsky et al., 1990, 1993). Fifty-four percent inhibition was achieved with $10^{-6}$M of NPF I indicating that NPF I affects trypsin biosynthesis in the gut by binding to a TMOF receptor and not by the release of neuroendocrine factors from the brain or the thoracic ganglia that in turn release TMOF from the ovary. Because the structure of NPF I is different from TMOF it appears that NPF I does not bind to TMOF specific binding site on the gut receptor but to a different site on the same or different receptor.

EXAMPLE 2

Effect of NPF Polypeptides on Mosquito Larvae

NPF polypeptides of the subject invention have been found to be highly effective pest control agents. NPF polypeptides sharing sequence homology with NPF I and NPF II of the Colorado potato beetle (*Leptinotarsa decemlineata*) (Spittaels, et al. Insect Biochem. Mol. Biol., 26(4):375–382, 1996) have been identified in the American cockroach (*Periplaneta americana*) (Veenstra and Lambrou, Biochem. Biophys. Res. Commun., 213(2):519–524, 1995), mosquito (*Aedes aegypti*) (Stanek et al., Display Presentation, Entomological Society of America Annual Meeting, Montreal, Canada, Dec. 3–6, 2000), and fruit fly (*Drosophila melanogaster*), and their pesticidal activity was confirmed. Synthesized polypeptides corresponding to the native polypeptides of Colorado potato beetle (SEQ ID NO. 1), mosquito (SEQ ID NOs. 5 and 7), American cockroach (SEQ ID NOs. 9 and 11), and fruit fly (SEQ ID NOs. 13 and 15) were provided to first instar *Aedes aegypti* larvae for ingestion. Non-amidated versions of SEQ ID NOs. 5, 7, 9, 11, 13, and 15 (SEQ ID NOs. 6, 8, 10, 12, 14, and 16, respectively), as well as other functional equivalents (SEQ ID NOs. 17–24), were also provided for ingestion.

First instar *Aedes aegypti* larvae were assayed in a microtiter plate in 188 $\mu$l solution containing 160 $\mu$l of water, 10 $\mu$l of 2% Brewer's yeast, and NPF polypeptides of the subject invention at concentrations of 2 mg/ml to 0.04 mg/ml (Table 2). Mortality was determined at 24 hour intervals for 3 to 7 days. Controls were run with yeast solution lacking the NPF polypeptide.

TABLE 2

Effect of NPF polypeptides on *Aedes aegypti* larvae

| SEQ ID NO. | NPF Polypeptide | $LC_{50}$ (mM) ± SEM |
|---|---|---|
| SEQ ID NO.1 | Ala-Arg-Gly-Pro-Gln-Leu-Arg-Leu-Arg-Phe-NH$_2$ (Mol.Wt.: 1211.30) | 0.65 ± 0.040 |
| SEQ ID NO.5 | Arg-Pro-Pro-Thr-Arg-Phe-Arg-Phe-NH$_2$ (Mol. Wt.: 1074.23) | 0.61 ± 0.018 |
| SEQ ID NO.6 | Arg-Pro-Pro-Thr-Arg-Phe-Arg-Phe-OH (Mol. Wt.: 1076.22) | 0.26 ± 10.02 |
| SEQ ID NO.7 | Ala-Pro-Gln-Leu-Arg-Leu-Arg-Phe-NH$_2$ (Mol. Wt.: 999.2) | 0.8 ± 0.06 |
| SEQ ID NO.8 | Ala-Pro-Gln-Leu-Arg-Leu-Arg-Phe-OH (Mol Wt.: 1000.18) | 0.65 ± 0.06 |
| SEQ ID NO.9 | Ala-Asn-Arg-Ser-Pro-Ser-Leu-Arg-Leu-Arg-Phe-NH$_2$ (Mol. Wt.: 1315.49) | 0.135 ± 0.06 |
| SEQ ID NO.10 | Ala-Asn-Arg-Ser-Pro-Ser-Leu-Arg-Leu-Arg-Phe-OH (Mol. Wt.: 1316.47) | 0.68 ± 0.037 |
| SEQ ID NO.11 | Ala-Asp-Arg-Ser-Pro-Ser-Leu-Arg-Leu-Arg-Phe-NH$_2$ (Mol. Wt.: 1315.47) | 0.65 ± 0.03 |
| SEQ ID NO.12 | Ala-Asp-Arg-Ser-Pro-Ser-Leu-Arg-Leu-Arg-Phe-OH (Mol. Wt.: 1317.45) | 0.607 ± 0.066 |
| SEQ ID NO.13 | Pro-Ile-Arg-Ser-Pro-Ser-Leu-Arg-Leu-Arg-Phe-NH$_2$ (Mol. Wt.: 1253.52) | 0.589 ± 0.04 |
| SEQ ID NO.14 | Pro-Ile-Arg-Ser-Pro-Ser-Leu-Arg-Leu-Arg-Phe-OH (Mol. Wt.: 1254.5) | 0.558 ± 0.03 |
| SEQ ID NO.15 | Ala-Gln-Arg-Ser-Pro-Ser-Leu-Arg-Leu-Arg-Phe-NH$_2$ (Mol. Wt.: 1329.52) | 1.03 ± 0.1 |

TABLE 2-continued

Effect of NPF polypeptides on Aedes aegypti larvae

| SEQ ID NO. | NPF Polypeptide | $LC_{50}$ (mM) ± SEM |
|---|---|---|
| SEQ ID NO.16 | Ala-Gln-Arg-Ser-Pro-Ser-Leu-Arg-Leu-Arg-Phe-OH (Mol. Wt.: 1330.5) | 1.187 ± 0.11 |
| SEQ ID NO.17 | Arg-Ser-Pro-Ser-Leu-Arg-Leu-Arg-Phe-$NH_2$ (Mol. Wt.: 1130.32) | 0.82 ± 0.07 |
| SEQ ID NO.18 | Arg-Ser-Pro-Ser-Leu-Arg-Leu-Arg-Phe-OH (Mol.Wt.: 1131.3) | 0.76 ± 0.04 |
| SEQ ID NO.19 | Pro-Ser-Leu-Arg-Leu-Arg-Phe-$NH_2$ (Mol. Wt.: 887.07) | >2.25 |
| SEQ ID NO 20 | Pro-Ser-Leu-Arg-Leu-Arg-Phe-OH (Mol. Wt.: 888.05) | 0.76 ± 0.051 |
| SEQ ID NO.21 | Leu-Arg-Leu-Arg-Phe-$NH_2$ (Mol. Wt.: 702.89) | >2.8 |
| SEQ ID NO.22 | Leu-Arg-Leu-Arg-Phe-OH (Mol. Wt.: 703.87) | 1.589 ± 0.143 |
| SEQ ID NO.23 | Arg-Pro-Pro-Thr-OH (Mol. Wt.: 469.52) | 2.08 ± 0.15 |
| SEQ ID NO.24 | Arg-Phe-Arg-Phe-OH (Mol. Wt.: 624.72) | 0.81 ± 0.06 |

EXAMPLE 3

Cytoimmunochemical Analysis

Cytoimmunochemical analysis of the mosquito gut after the blood meal using antiserum against NPF I revealed that exocrine cells with NPF I-like molecules are synthesized by the mosquito epithelial cells 24 hours after a blood meal. In females that did not take a blood meal these cells are not found. Thus, it is possible that NPF I is a secondary signal in a cascade of signals that starts with the release of TMOF from the ovary, the hormone then birids to a TMOF gut receptor (Borovsky et al., 1994) that stimulates the synthesis and release of NPF I from gut specific exocrine cells. NPF I binds to a receptor NPF I binds to a receptor site on the gut the binding site may be adjacent to or part of the TMOF receptor and causes the cessation of trypsin biosynthesis.

EXAMPLE 4

Bioassays for Activity Against Lepidopteron and Coleopterans

Biological activity of the pest control compounds of the subject invention can be confirmed using standard bioassay procedures. One such assay is the budworm-bollworm (*Heliothis virescens* [Fabricius] and *Helicoverpa zea* [Boddie]) assay. Lepidoptera bioassays can be conducted with either surface application to artificial insect diet or diet incorporation of samples. All Lepidopteran insects can be tested from the neonate stage to the second instar. All assays can be conducted with either toasted soy flour artificial diet or black cutworm artificial diet (BioServ, Frenchtown, N.J.).

Diet incorporation can be conducted by mixing the samples containing the pest-control compound with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no pest control compound serves as the control. First instar larvae (USDA-ARS, Stoneville, Miss.) are placed onto the diet mixture. Wells are then sealed with Mylar sheeting (ClearLam Packaging, Ill.) using a tacking iron, and several pinholes are made in each well to provide gas exchange. Larvae can be held at 25° C. for 6 days in a 14:10 (light:dark) holding room. Mortality and stunting are then recorded after six days.

Bioassay by the top load method utilizes the same sample and diet preparations as listed above. The samples are applied to the surface of the insect diet. In a specific embodiment, surface area can range from 0.3 to approximately 0.8 $cm^2$ depending on the tray size; 96 well tissue culture plates can be used in addition to the format listed above. Following application, samples are allowed to air dry before insect infestation. A water blank containing no control compound can serve as the control. Eggs are applied to each treated well. The wells are then sealed with Mylar sheeting (ClearLam Packaging, Ill.) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of the pest control sample onto an agar-based artificial diet at a rate of 160 ml/$cm^2$. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays are held in darkness at 25° C., and mortality scored after four days.

Analogous bioassays can be performed by those skilled in the art to assess activity against other pests, such as the black cutworm (*Agrotis epsilon*).

EXAMPLE 5

Target Pests

Toxins of the subject invention can be used, alone or in combination with other toxins, to control one or more non-mammalian pests. These pests may be, for example, those listed in Table 3. Activity can readily be confirmed using the bioassays provided herein, adaptations of these bioassays, and/or other bioassays well known to those skilled in the art.

TABLE 3

Target pest species

| ORDER/Common Name | Latin Name |
| --- | --- |
| *LEPIDOPTERA* | |
| European Corn Borer | *Ostrinia nubilalis* |
| European Corn Borer resistant to Cry1A | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Spilosoma | *Spilosoma virginica* |
| Bertha Armyworm | *Mamestra configurata* |
| Diamondback Moth | *Plutella xylostells* |
| *COLEOPTERA* | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| *DIPTERA* | |
| Hessian Fly | *Mayetiola destructor* |
| *HOMOPTERA* | |
| Greenbug | *Schizaphis graminum* |
| *HEMIPTERA* | |
| Lygus Bug | *Lygus lineolaris* |
| *NEMATODA* | *Heterodera glycines* |

EXAMPLE 6

Insertion of Toxin Genes Into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *Bacillus* toxin can be inserted into the vector at a suitable restriction site. The resulting plasmid is used to transform *E. coli*. The *E. coli* cells are cultivated in a suitable nutrient medium, then harvested and lysed. The plasmid is recovered. Sequence analysis, restriction analysis, electrophoresis, and other biochemical and/or molecular biological methods are generally carried out as methods of analysis. After each manipulation, the DNA sequence used can be cleaved and joined to the next DNA sequence. Each plasmid sequence can be cloned in the same or other plasmids. Once the inserted DNA has been integrated in the genome, it is relatively stable there and, as a rule, does not come out again. It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. These techniques include transformation with T-DNA ("transferred DNA"; discussed in more detail below) using *Agrobacterium tumefaciens* or *Agrobacterium rhizogenes* as transformation agent, fusion, injection, biolistics (microparticle bombardment), or electroporation and other methods known to those of skill in the art.

One of the most widely used approaches for the introduction of DNA into plant cells exploits the natural DNA-transferring properties of *Agrobacterium tumefacients* and *Agrobacterium rhizogenes*, the two species which cause crown gall and hairy root. Their ability to cause disease depends on the presence of large plasmids, in excess of 100 kb, which are referred to as the "Tumour-inducing" or (Ti) and "Root-inducing" (or Ri) plasmids respectively.

A region referred to as the T-DNA ("Transferred DNA") is transferred from an infecting *Agrobacterium* cell into the nucleus of the plant cell, where it is integrated into the plant genome. Transfer of the T-DNA depends on a set of genes called vir if they are on the Ti plasmid, or chv if they are on the chromosome. These genes are induced in response to various compounds in exudates from wounded plants. The T-DNA itself is flanked by repeated sequences of around 25 base pairs, called border repeats (or left and right borders). The T-DNA contains a group of genes referred to as the onc genes, which are responsible for the oncogenicity of the T-DNA.

The use of *Agrobacterium* in the genetic manipulation of plants involves the insertion of foreign DNA into the T-DNA of a bacterial cell and subsequent transfer of the DNA by the transformed bacterium into the plant. As long as the necessary proteins are provided by the bacterium, any sequences flanked by the T-DNA border repeats can be transferred into the recipient plant cell genome. The Ti plasmids are too large to manipulate directly, but this problem can be circumvented by using cointegrative and binary systems.

The two main components of a cointegrative system are a Ti plasmid that has typically been modified by the replacement of material between the border repeats (including the onc sequences) by pBR322; and a intermediate vector, which is a modified pBR322 containing an extra marker, such as kanamycin resistance. The gene to be introduced into the target plant is first cloned in to the intermediate vector, and this construct is then introduced into *Agrobacterium* containing the Ti vector. The pBR322-based plasmid cannot replicate efficiently inside *Agrobacterium*, so selection for kanamycin resistance identifies those *Agrobacterium* cells where the pBR322-based intermediate plasmid has been integrated by homologous recombination into the Ti plasmid. Because the recombination is homologous, it will take place across the pBR322 sequences and therefore result in integration between the border repeats.

The need for cointegration of the plasmids can be circumvented by use of a binary vector, such as pBin19, a small plasmid containing a pair of left and right borders. The lacZ region, located within the borders, facilitates insertion and detection of DNA. A neomycin phosphotransferase gene, typically modified for expression in plants by addition of nopalline synthase expression sequences, is also present within the borders. Outside the left and right borders, there is typically a kanamycin resistance gene that will function in prokaryotes and a broad host-range origin derived from the plasmid pRK252. The proteins that catalyze transfer of the T-DNA into the host plant do not have to be cis-encoded (i.e., do not have to be encoded by the same molecule). Therefore, if the binary vector is introduced into *Agrobacterium* that already contains a resident Ti plasmid, the resident plasmid can provide all the functions needed to transfer into a plant nucleus the DNA between the borders of the binary vector.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of controlling a pest wherein said method comprises applying to the pest, or to a pest-inhabited locus, transformed cells expressing an exogenous polynucleotide encoding a pesticidal polypeptide, wherein the pesticidal polypeptide comprises an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO;14, SEQ ID NO:16, SEQ ID NO:18, SEQ ID NO:20, SEQ ID NO:22, SEQ ID NO:23, and SEQ ID NO:24, and wherein the pest ingests the pesticidal polypeptide.

2. The method of claim 1, wherein the pesticidal polypeptide comprises the amino acid sequence of SEQ ID NO:3.

3. The method of claim 1, wherein the pesticidal polypeptide comprises the amino acid sequence of SEQ ID NO. 4.

4. The method of claim 1, wherein the pesticidal polypeptide comprises an amino acid sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

5. The method of claim 1, wherein the pesticidal polypeptide is a fusion polypeptide.

6. The method of claim 5, wherein the fusion polypeptide is a multimer or the amino acid sequence.

7. The method of claim 1, wherein the cells are pest food cells comprising the polynucleotide encoding the pesticidal polypeptide.

8. The method of claim 1, wherein the cells are algae cells.

9. The method of claim 1, wherein the cells are a *Clorella* species.

10. The method of claim 1, wherein the cells are yeast cells.

11. The method of claim 1, wherein the cells are applied in a living state.

12. The method of claim 1, wherein the cells are applied in a non-living state.

13. The method of claim 1, wherein the cells are applied as a component of a pesticidal composition which also comprises a pesticidally acceptable carrier.

14. The method of claim 1, wherein the pest utilizes a serine esterase as a digestive enzyme, and wherein the pesticidal polypeptide inhibits synthesis of the serine esterase within the pest.

15. The method of claim 1, wherein the pest utilizes trypsin as a digestive enzyme, and wherein the pesticidal polypeptide inhibits synthesis of the trypsin within the pest.

16. The method of claim 1, wherein the pest is selected from the group consisting of coleopterans, lepidopterans, and dipterans.

17. The method of claim 1, wherein the pest is a blood-sucking pest.

18. The method of claim 1, wherein the pest is of the suborder Nematocera.

19. The method of claim 1, wherein the pest is a pest of the family Colicidae.

20. The method of claim 1, wherein the pest is a dipteran.

21. The method of claim 1, wherein the pest is of a genus selected from the group consisting of *Heliothis, Culex, Theobaldia, Aedes, Anopheles, Forciponiyia, Culicoides* and *Helea.*

22. The method of claim 1, wherein the pest is selected from the group consisting of mosquitoes, flesh flies, fleas, sand flies, house flies, and dog flies.

23. The method of claim 1, wherein the pest is a mosquito.

24. The method of claim 1, wherein the pest is of a species selected from the group consisting of: *Aedes aegypti, Culex quinquefasciatus, Anopheles albimanus, Anopheles quadrimaculatus, Lutzomyia anthrophora, Culicoides variipennis, Stomoxys calcitrans, Musca domestica, Ctenocephalides felis*, and *Heliothis virescens.*

25. The method of claim 1, wherein said method comprises applying the cells to a pest-inhabited locus.

26. The method of claim 25, wherein the pest-inhabited locus is a body of water.

27. The method of claim 1, wherein the cells are applied in association with a pest food.

28. A method for preparing a pesticidal composition comprising transforming a host cell with an exogenous polynucleotide encoding a pesticidal polypeptide, operatively linked to a promoter, and bringing the transformed host cell into association with a pesticidally acceptable carrier, wherein the pesticidal polypeptide comprises an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

29. The method of claim 28, wherein the pesticidal polypeptide comprises the amino acid sequence of SEQ ID NO:3.

30. The method of claim 28, wherein the pesticidal polypeptide comprises the amino acid sequence of SEQ ID NO:4.

31. The method of claim 28, wherein the pesticidal polypeptide comprises an amino acid sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:21, SEQ ID NO:22, SEQ ID NO:23, and SEQ ID NO:24.

32. The method of claim 28, wherein the pesticidal polypeptide is a fusion polypeptide.

33. The method of claim 32, wherein the fusion polypeptide is a multimer of the amino acid sequence.

34. An expression vector comprising a promoter and a polynucleotide encoding a pesticidal polypeptide wherein the promoter has the capacity to control expression of said polynucleotide in a host cell, and wherein said pesticidal polypeptide comprises an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

35. The expression vector of claim 34, wherein said pesticidal polypeptide comprises the amino acid of SEQ ID NO:3.

36. The expression vector of claim 34, wherein said pesticidal polypeptide comprises the amino acid of SEQ ID NO:4.

37. The expression vector of claim 34, wherein said pesticidal polypeptide comprises an amino acid sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

38. The expression vector of claim 34, wherein said pesticidal polypeptide is a fusion polypeptide.

39. The expression vector of claim 38, wherein said fusion polypeptide is a multimer of said amino acid sequence.

40. A transformed cell comprising an exogenous polynucleotide encoding a pesticidal polypeptide, operatively linked to a promoter, wherein said cell expresses said polynucleotide to produce said pesticidal polypeptide, and wherein said pesticidal polypeptide comprises an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

41. The transformed cell of claim 40, wherein said pesticidal polypeptide comprises the amino acid sequence of SEQ ID NO:3.

42. The transformed cell of claim 40, wherein said pesticidal polypeptide comprises the amino acid sequence of SEQ ID NO:4.

43. The transformed cell of claim 40, wherein said pesticidal polypeptide comprises the amino acid sequence of SEQ ID NO:6.

44. The transformed cell of claim 40, wherein said pesticidal polypeptide comprises the amino acid sequence of SEQ ID NO:8.

45. The transformed cell of claim 40, wherein said pesticidal polypeptide comprises the amino acid sequence of SEQ ID NO:10.

46. The transformed cell of claim 40, wherein said pesticidal polypeptide comprises the amino acid sequence of SEQ ID NO:12.

47. The transformed cell of claim 40, wherein said pesticidal polypeptide comprises the amino acid sequence of SEQ ID NO:14.

48. The transformed cell of claim 40, wherein said pesticidal polypeptide comprises the amino acid sequence of SEQ ID NO:16.

49. The transformed cell of claim 40, wherein said pesticidal polypeptide comprises the amino acid sequence of SEQ ID NO:18.

50. The transformed cell of claim 40, wherein said pesticidal polypeptide comprises the amino acid sequence of SEQ ID NO:20.

51. The transformed cell of claim 40, wherein said pesticidal polypeptide comprises the amino acid sequence of SEQ ID NO:22.

52. The transformed cell of claim 40, wherein said pesticidal polypeptide comprises the amino acid sequence of SEQ ID NO:23.

53. The transformed cell of claim 40, wherein said pesticidal polypeptide comprises the amino acid sequence of SEQ ID NO:24.

54. The transformed cell of claim 40, wherein the transformed cell is a pest food.

55. The transformed cell of claim 40, wherein the transformed cell is mosquito larvae food.

56. The transformed cell of claim 40, wherein the transformed cell is an algae cell.

57. The transformed cell of claim 40, wherein the transformed cell is a green algae cell.

58. The transformed cell of claim 40, wherein the transformed cell is a *Clorella* species.

59. The transformed cell of claim 40, wherein the transformed cell is a yeast cell.

60. A pesticidal composition comprising: transformed cells expressing an exogenous polynucleotide encoding a pesticidal polypeptide, operatively linked to a promoter, wherein said pesticidal polypeptide comprises an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24; and a pesticidally acceptable carrier.

61. The pesticidal composition of claim 60, wherein said pesticidal polypeptide comprises the amino acid sequence of SEQ ID NO:3.

62. The pesticidal composition of claim 60, wherein said pesticidal polypeptide comprises the amino acid sequence of SEQ ID NO:4.

63. The pesticidal composition of claim 60, wherein said pesticidal polypeptide comprises an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

64. The pesticidal composition of claim 60, wherein said composition is in a form selected from the group consisting of pellets, briquettes, bricks, powders, granules, sprays, solutions and capsules.

65. The pesticidal composition of claim 60, wherein said composition is formulated to float on an aqueous medium.

66. The pesticidal composition of claim 60, wherein said composition is formulated to maintain a depth of 0 to 2 feet below the surface of an aqueous medium.

67. The pesticidal composition of claim 60, wherein said composition is formulated to sink in an aqueous medium.

68. An expression vector comprising a promoter and a polynucleotide encoding a pesticidal polypeptide wherein the promoter has the capacity to control expression of said polynucleotide in a host cell, and wherein the pesticidal polypeptide consists of an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

69. A transformed cell comprising an exogenous polynucleotide encoding a pesticidal polypeptide, operatively linked to a promoter, wherein said cell expresses said polynucleotide to produce said pesticidal polypeptide, and wherein said pesticidal polypeptide consists of an amino acid sequence selected from the group consisting of SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:23, and SEQ ID NO:24.

* * * * *

UNITED STATES PATENT AND TRADEMARK OFFICE
CERTIFICATE OF CORRECTION

PATENT NO. : 6,884,878 B2
DATED : April 26, 2005
INVENTOR(S) : Dov Borovsky, Arnold De Loof and Peter Verhaert It is certified that error appears in the above-identified patent and that said Letters Patent is hereby corrected as shown below:

Column 19,
Line 42, "then birids to" should read -- then binds to --.

Column 35,
Line 36, "multimer or" should read -- multimer of --.

Signed and Sealed this

Twenty-third Day of August, 2005

JON W. DUDAS
*Director of the United States Patent and Trademark Office*

SEQUENCE LISTING

<160> NUMBER OF SEQ ID NOS: 28

<210> SEQ ID NO 1
<211> LENGTH: 10
<212> TYPE: PRT
<213> ORGANISM: Colorado potato beetle
<220> FEATURE:
<221> NAME/KEY: Amidation
<222> LOCATION: (10)..(10)
<223> OTHER INFORMATION: Amidated Phenylalanine

<400> SEQUENCE: 1

Ala Arg Gly Pro Gln Leu Arg Leu Arg Phe
1               5                   10

<210> SEQ ID NO 2
<211> LENGTH: 8
<212> TYPE: PRT
<213> ORGANISM: Colorado potato beetle
<220> FEATURE:
<221> NAME/KEY: Amidation
<222> LOCATION: (8)..(8)
<223> OTHER INFORMATION: Amidated Phenylalanine

<400> SEQUENCE: 2

Ala Pro Ser Leu Arg Leu Arg Phe
1               5

<210> SEQ ID NO 3
<211> LENGTH: 10
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(10)
<223> OTHER INFORMATION: Non-amidated amino acids

<400> SEQUENCE: 3

Ala Arg Gly Pro Gln Leu Arg Leu Arg Phe
1               5                   10

<210> SEQ ID NO 4
<211> LENGTH: 8
<212> TYPE: PRT
<213> ORGANISM: Artificial Sequence

```
<220> FEATURE:
<223> OTHER INFORMATION: NPF peptide
<220> FEATURE:
<221> NAME/KEY: Variant
<222> LOCATION: (1)..(8)
<223> OTHER INFORMATION: Non-amidated amino acids

<400> SEQUENCE: 4

Ala Pro Ser Leu Arg Leu Arg Phe
 1               5

<210> SEQ ID NO 5
<211> LENGTH: 8
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (8)..(8)
<223> OTHER INFORMATION: Amidated Phenylalanine

<400> SEQUENCE: 5

Arg Pro Pro Thr Arg Phe Arg Phe
 1               5

<210> SEQ ID NO 6
<211> LENGTH: 8
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(8)
<223> OTHER INFORMATION: Non-amidated amino acids

<400> SEQUENCE: 6

Arg Pro Pro Thr Arg Phe Arg Phe
 1               5

<210> SEQ ID NO 7
<211> LENGTH: 8
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (8)..(8)
<223> OTHER INFORMATION: Amidated Phenylalanine

<400> SEQUENCE: 7

Ala Pro Gln Leu Arg Leu Arg Phe
 1               5

<210> SEQ ID NO 8
<211> LENGTH: 8
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(8)
<223> OTHER INFORMATION: Non-amidated amino acids

<400> SEQUENCE: 8

Ala Pro Gln Leu Arg Leu Arg Phe
 1               5
```

<210> SEQ ID NO 9
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (11)..(11)
<223> OTHER INFORMATION: Amidated Phenylalanine

<400> SEQUENCE: 9

Ala Asn Arg Ser Pro Ser Leu Arg Leu Arg Phe
1               5                   10

<210> SEQ ID NO 10
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(11)
<223> OTHER INFORMATION: Non-amidated amino acids

<400> SEQUENCE: 10

Ala Asn Arg Ser Pro Ser Leu Arg Leu Arg Phe
1               5                   10

<210> SEQ ID NO 11
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (11)..(11)
<223> OTHER INFORMATION: Amidated Phenylalanine

<400> SEQUENCE: 11

Ala Asp Arg Ser Pro Ser Leu Arg Leu Arg Phe
1               5                   10

<210> SEQ ID NO 12
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(11)
<223> OTHER INFORMATION: Non-amidated amino acids

<400> SEQUENCE: 12

Ala Asp Arg Ser Pro Ser Leu Arg Leu Arg Phe
1               5                   10

<210> SEQ ID NO 13
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (11)..(11)

<223> OTHER INFORMATION: Amidated Phenylalanine

<400> SEQUENCE: 13

Pro Ile Arg Ser Pro Ser Leu Arg Leu Arg Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(11)
<223> OTHER INFORMATION: Non-amidated amino acids

<400> SEQUENCE: 14

Pro Ile Arg Ser Pro Ser Leu Arg Leu Arg Phe
1               5                   10

<210> SEQ ID NO 15
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (11)..(11)
<223> OTHER INFORMATION: Amidated Phenylalanine

<400> SEQUENCE: 15

Ala Gln Arg Ser Pro Ser Leu Arg Leu Arg Phe
1               5                   10

<210> SEQ ID NO 16
<211> LENGTH: 11
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(11)
<223> OTHER INFORMATION: Non-amidated amino acids

<400> SEQUENCE: 16

Ala Gln Arg Ser Pro Ser Leu Arg Leu Arg Phe
1               5                   10

<210> SEQ ID NO 17
<211> LENGTH: 9
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (9)..(9)
<223> OTHER INFORMATION: Amidated Phenylalanine

<400> SEQUENCE: 17

Arg Ser Pro Ser Leu Arg Leu Arg Phe
1               5

<210> SEQ ID NO 18
<211> LENGTH: 9
<212> TYPE: PRT

```
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(9)
<223> OTHER INFORMATION: Non-amidated amino acids

<400> SEQUENCE: 18

Arg Ser Pro Ser Leu Arg Leu Arg Phe
1               5

<210> SEQ ID NO 19
<211> LENGTH: 7
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (7)..(7)
<223> OTHER INFORMATION: Amidated Phenylalanine

<400> SEQUENCE: 19

Pro Ser Leu Arg Leu Arg Phe
1               5

<210> SEQ ID NO 20
<211> LENGTH: 7
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(7)
<223> OTHER INFORMATION: Non-amidated amino acids

<400> SEQUENCE: 20

Pro Ser Leu Arg Leu Arg Phe
1               5

<210> SEQ ID NO 21
<211> LENGTH: 5
<212> TYPE: PRT
<213> ORGANISM: Artificial Sequence
<220> FEATURE:
<223> OTHER INFORMATION: NPF peptide
<220> FEATURE:
<221> NAME/KEY: Amidation
<222> LOCATION: (5)..(5)
<223> OTHER INFORMATION: Amidated Phenylalanine

<400> SEQUENCE: 21

Leu Arg Leu Arg Phe
1               5

<210> SEQ ID NO 22
<211> LENGTH: 5
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(5)
<223> OTHER INFORMATION: Non-amidated amino acids

<400> SEQUENCE: 22

Leu Arg Leu Arg Phe
```

```
<210> SEQ ID NO 23
<211> LENGTH: 4
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(4)
<223> OTHER INFORMATION: Non-amidated amino acids

<400> SEQUENCE: 23

Arg Pro Pro Thr
1

<210> SEQ ID NO 24
<211> LENGTH: 4
<212> TYPE: PRT
<213> ORGANISM: Artificial Sequence
<220> FEATURE:
<223> OTHER INFORMATION: NPF peptide
<220> FEATURE:
<221> NAME/KEY: Variant
<222> LOCATION: (1)..(4)
<223> OTHER INFORMATION: Non-amidated amino acids

<400> SEQUENCE: 24

Arg Phe Arg Phe
1

<210> SEQ ID NO 25
<211> LENGTH: 5
<212> TYPE: PRT
<213> ORGANISM: Artificial Sequences
<220> FEATURE:
<223> OTHER INFORMATION: TMOF peptide

<400> SEQUENCE: 25

Tyr Asp Pro Ala Pro
1               5

<210> SEQ ID NO 26
<211> LENGTH: 6
<212> TYPE: PRT
<213> ORGANISM: Artificial Sequence
<220> FEATURE:
<223> OTHER INFORMATION: TMOF peptide

<400> SEQUENCE: 26

Tyr Asp Pro Ala Pro Pro
1               5

<210> SEQ ID NO 27
<211> LENGTH: 7
<212> TYPE: PRT
<213> ORGANISM: Artificial Sequence
<220> FEATURE:
<223> OTHER INFORMATION: TMOF peptide

<400> SEQUENCE: 27

Tyr Asp Pro Ala Pro Pro Pro
1               5

<210> SEQ ID NO 28
<211> LENGTH: 8
<212> TYPE: PRT
```

```
-continued
<213> ORGANISM: Artificial Sequence
<220> FEATURE:
<223> OTHER INFORMATION: TMOF peptide

<400> SEQUENCE: 28

Tyr Asp Pro Ala Pro Pro Pro Pro
1               5
```